United States Patent
Hu et al.

(10) Patent No.: US 10,709,732 B2
(45) Date of Patent: Jul. 14, 2020

(54) HYPERTONIC PHARMACEUTICAL COMPOSITIONS CONTAINING AN ANTI-PLATINUM CHEMOPROTECTANT AGENT

(71) Applicant: Decibel Therapeutics, Inc., Boston, MA (US)

(72) Inventors: Qi-Ying Hu, Needham, MA (US); John Lee, Arlington, MA (US); Fuxin Shi, Winchester, MA (US)

(73) Assignee: Decibel Therapeutics, Inc., Boston, MA (US)

( * ) Notice: Subject to any disclaimer, the term of this patent is extended or adjusted under 35 U.S.C. 154(b) by 0 days.

(21) Appl. No.: 16/517,284

(22) Filed: Jul. 19, 2019

(65) Prior Publication Data

US 2019/0336524 A1   Nov. 7, 2019

Related U.S. Application Data

(63) Continuation of application No. PCT/US2019/017334, filed on Feb. 8, 2019.

(60) Provisional application No. 62/628,824, filed on Feb. 9, 2018.

(51) Int. Cl.
*A61K 33/04* (2006.01)
*A61K 9/00* (2006.01)
*A61K 47/36* (2006.01)

(52) U.S. Cl.
CPC ............ *A61K 33/04* (2013.01); *A61K 9/0019* (2013.01); *A61K 9/0046* (2013.01); *A61K 47/36* (2013.01)

(58) Field of Classification Search
CPC ...... A61K 33/04; A61K 47/36; A61K 9/0019; A61K 9/0046
See application file for complete search history.

(56) References Cited

U.S. PATENT DOCUMENTS

| | | | |
|---|---|---|---|
| 6,497,902 B1 | 12/2002 | Ma | |
| 6,649,621 B2 | 11/2003 | Kopke et al. | |
| 7,790,699 B2 | 9/2010 | Melvik et al. | |
| 8,496,957 B2 | 7/2013 | Lichter et al. | |
| 8,784,870 B2 | 7/2014 | Lichter et al. | |
| 9,427,472 B2 | 8/2016 | Lichter et al. | |
| 9,944,524 B2 | 4/2018 | Sherman et al. | |
| 10,272,034 B2 | 4/2019 | Lichter et al. | |
| 2004/0186172 A1 | 9/2004 | Ibrahim | |
| 2013/0045957 A1 | 2/2013 | Piu et al. | |
| 2013/0085476 A1 | 4/2013 | Imran | |
| 2017/0182089 A1 | 6/2017 | Neuwelt et al. | |
| 2018/0161297 A1 | 6/2018 | Kirnon et al. | |
| 2018/0228903 A1 | 8/2018 | Kohane et al. | |
| 2018/0360874 A1 | 12/2018 | Nivoliez | |
| 2019/0144276 A1 | 5/2019 | Sherman et al. | |
| 2019/0160094 A1 | 5/2019 | Neuwelt | |
| 2019/0192425 A1 | 6/2019 | Lichter et al. | |

FOREIGN PATENT DOCUMENTS

| | | |
|---|---|---|
| WO | WO-2017/139684 A1 | 8/2017 |
| WO | WO-2018/136605 A1 | 7/2018 |
| WO | WO-2019/108592 A2 | 6/2019 |
| WO | WO-2019/118330 A1 | 6/2019 |
| WO | WO-2019/126783 A1 | 6/2019 |
| WO | WO-2019/140012 A1 | 7/2019 |
| WO | WO-2019154895 A1 | 8/2019 |
| WO | WO-2019/210107 A1 | 10/2019 |
| WO | WO-2019/244121 A1 | 12/2019 |

OTHER PUBLICATIONS

Pestieau et al., "Impact of carrier solutions on pharmacokinetics of intraperitoneal chemotherapy," Cancer Chemother Pharmacol. 47(3):269-76 (2001) (Abstract Only) (2 pages).
Wu et al., "The chemoprotective agent N-acetylcysteine blocks cisplatin-induced apoptosis through caspase signaling pathway," J Pharmacol Exp Ther 312(2):424-31 (2005).
International Search Report and Written Opinion for International Patent Application No. PCT/US2019/017334 dated May 7, 2019 (20 pages).
Choi et al., "Perilymph osmolality modulates cochlear function," available in PMC Mar. 14, 2013, published in final edited form as: Laryngoscope. 118(9):1621-9 (2008) (16 pages).
Meyer et al., "Randomized controlled trial to test the efficacy of transtympanic injections of a sodium thiosulfate gel to prevent cisplatin-induced ototoxicity," J Clin Oncol. 35(15): Supp. Supplement 1 (2017) (Abstract only) (2 pages).
Rolland et al., "A randomized controlled trial to test the efficacy of trans-tympanic injections of a sodium thiosulfate gel to prevent cisplatin-induced ototoxicity in patients with head and neck cancer," J Otolaryngol Head Neck Surg. 48(1):4 (2019) (9 pages).
U.S. Appl. No. 16/427,567, Decibel Therapeutics, Inc.
Andersson et al., "Pharmacokinetics of cisplatin and its monohydrated complex in humans," J Pharm Sci. 85(8):824-7 (1996).
Berglin et al., "Prevention of cisplatin-induced hearing loss by administration of a thiosulfate-containing gel to the middle ear in a guinea pig model," Cancer Chemother Pharmacol. 68(6):1547-56 (2011).
Freyer et al., "Interventions for cisplatin-induced hearing loss in children and adolescents with cancer," Lancet Child Adolesc Health. doi: 10.1016/S2352-4642(19)30115-4 (2019) (7 pages).
Johnsson et al., "Pharmacokinetics and tissue distribution of cisplatin in nude mice: platinum levels and cisplatin-DNA adducts," Cancer Chemother Pharmacol. 37(1-2):23-31 (1995).
Khunmanee et al., "Crosslinking method of hyaluronic-based hydrogel for biomedical applications," J Tissue Eng. 8:1-16 (2017).

(Continued)

*Primary Examiner* — Robert S Cabral
(74) *Attorney, Agent, or Firm* — Clark & Elbing LLP

(57) ABSTRACT

Hypertonic pharmaceutical compositions are disclosed. The hypertonic pharmaceutical compositions contain an anti-platinum chemoprotectant agent and a gelling agent. Also disclosed are methods of medical use of the hypertonic pharmaceutical compositions.

33 Claims, 5 Drawing Sheets

(56) References Cited

OTHER PUBLICATIONS

Leitao et al., "Quantification of sodium thiosulphate protection on cisplatin-induced toxicities," J Otolaryngol. 32(3):146-50 (2003).

Otto et al., "Effects of cisplatin and thiosulfate upon auditory brainstem responses of guinea pigs," Hear Res. 35(1):79-85 (1988).

Pierre, Pernilla, Thesis: "Cisplatin, a platinum-containing antineoplastic drug: perspectives on analytical chemistry and prevention of ototoxicity," Department of Oncology-Pathology, Karolinska Institutet, 2010.

Pierre et al., "Middle ear administration of a particulate chitosan gel in an in vivo model of cisplatin ototoxicity," Front Cell Neurosci. 13(268): (2019) (13 pages).

Schroeder II et al., "Pharmacokinetics of sodium thiosulfate in guinea pig perilymph following middle ear application," J Otol. 13(2):54-8 (2018).

Togawa et al., "High performance liquid chromatographic determination of bound sulfide and sulfite and thiosulfate at their low levels in human serum by pre-column fluorescence derivatization with monobromobimane," Chem Pharm Bull. 40(11):3000-4 (1992).

Urien et al., "Population pharmacokinetics of total and unbound plasma cisplatin in adult patients," Br J Clin Pharmacol. 57(6):756-63 (2004).

Wang et al., "Local application of sodium thiosulfate prevents cisplatin-induced hearing loss in the guinea pig," Neuropharmacology. 45(3):380-93 (2003).

"Cisplatin With or Without Sodium Thiosulfate in Treating Young Patients With Stage I, II, or III Childhood Liver Cancer (SIOPEL 6)," US National Library of Medicine, <https://clinicaltrials.gov/ct2/show/study/NCT00652132>, retrieved on Dec. 11, 2018 (2015) (9 pages).

Wang, "Tolerability of hypertonic injectables," Int J Pharm. 490(1-2):308-15 (2015).

Mean±SEM; Two-Way ANOVA—LE vs RE or LE vs veh LE

Cisplatin 10MPK, intravenous (IV) injection

HYPERTONIC PHARMACEUTICAL COMPOSITIONS CONTAINING AN ANTI-PLATINUM CHEMOPROTECTANT AGENT

FIELD OF THE INVENTION

The present invention provides pharmaceutical compositions containing an anti-platinum chemoprotectant agent, methods of using the same, and methods of their preparation.

BACKGROUND

Platinum-based antineoplastic agents (e.g., cisplatin) are chemotherapeutic agents widely used to treat cancers and tumors. These agents are toxic and are known to induce hearing loss both in human and animal models. Thus, patients undergoing chemotherapy with platinum-based antineoplastic agents can suffer from hearing loss. There is a need for otoprotective compositions and methods to prevent or mitigate hearing loss associated with chemotherapeutic regimens including platinum-based antineoplastic agents.

SUMMARY OF THE INVENTION

In general, the invention provides pharmaceutical compositions (e.g., hypertonic pharmaceutical compositions) and methods of their use for preventing or mitigating platinum-induced ototoxicity.

In one aspect, the invention provides a pharmaceutical composition (e.g., a hypertonic pharmaceutical composition) containing an anti-platinum chemoprotectant agent and a gelling agent.

In some embodiments, the calculated osmolarity of the composition is at least 400 mOsm/L (e.g., at least 500 mOsm/L, at least 600 mOsm/L, at least 700 mOsm/L, at least 800 mOsm/L, at least 900 mOsm/L, at least 1,000 mOsm/L, at least 1,500 mOsm/L, at least 2,000 mOsm/L, at least 2,500 mOsm/L, or at least 3,000 mOsm/L). In certain embodiments, the calculated osmolarity of the composition is 5,000 mOsm/L or less (e.g., 4,500 mOsm/L or less, 4,000 mOsm/L or less, 3,000 mOsm/L or less, 2,000 mOsm/L or less, 1,800 mOsm/L or less, 1,500 mOsm/L or less, 1,200 mOsm/L or less, or 1,000 mOsm/L or less). In some embodiments, the calculated osmolarity of the composition is 1,500-4,500 mOsm/L. In other embodiments, the calculated osmolarity of the composition is 3,000-4,500 mOsm/L. In particular embodiments, the measured osmolality of the composition is at least 0.3 Osm/kg (e.g., at least 0.5 Osm/kg, at least 0.6 Osm/kg, at least 0.7 Osm/kg, at least 0.8 Osm/kg, at least 0.9 Osm/kg, at least 1.0 Osm/kg, at least 1.2 Osm/kg, at least 1.4 Osm/kg, or at least 1.8 Osm/kg). In further embodiments, the measured osmolality of the composition is 2.5 Osm/kg or less (e.g., 2.1 Osm/kg or less). In yet further embodiments, the measured osmolality of the composition is 0.3-2.5 Osm/kg (e.g., 0.5-2.5 Osm/kg, 0.6-2.5 Osm/kg, 0.7-2.5 Osm/kg, 0.8-2.5 Osm/kg, 0.9-2.5 Osm/kg, 1.0-2.5 Osm/kg, 1.2-2.5 Osm/kg, 1.4-2.5 Osm/kg, 1.8-2.5 Osm/kg, 0.5-2.1 Osm/kg, 0.6-2.1 Osm/kg, 0.7-2.1 Osm/kg, 0.8-2.1 Osm/kg, 0.9-2.1 Osm/kg, 1.0-2.1 Osm/kg, 1.2-2.1 Osm/kg, 1.4-2.1 Osm/kg, or 1.8-2.1 Osm/kg).

In particular embodiments, the anti-platinum chemoprotectant agent is an alkaline or ammonium thiosulfate salt or solvate thereof, an alkaline diethyldithiocarbamate salt, amifostine, methionine, N-acetylcysteine, cysteine, 2-aminoethanethiol, glutathione (GSH) or a $C_1$-$C_6$ alkyl ester thereof, lysine, histidine, arginine, ethylene diamine tetraacetic acid, dimercaprol, dimercaptosuccinic acid, dimercapto-propane sulfonate salt, penicillamine, α-lipoic acid, or fursultiamine, or a salt thereof. In further embodiments, the anti-platinum chemoprotectant agent is an alkaline or ammonium thiosulfate salt or a solvate thereof (e.g., sodium thiosulfate or a solvate thereof).

In yet further embodiments, the gelling agent is hyaluronan, a polyoxyethylene-polyoxypropylene block copolymer (e.g., a poloxamer), poly(lactic-co-glycolic) acid, polylactic acid, polycaprolactone, alginic acid or a salt thereof, polyethylene glycol, a cellulose, a cellulose ether (e.g., methylcellulose, carboxymethylcellulose, ethylcellulose, hydroxyethylcellulose, methyl hydroxyethylcellulose, hydroxypropyl methylcellulose, or hydroxypropylcellulose), a carbomer (e.g., Carbopol®), agar-agar, gelatin, glucomannan, galactomannan (e.g., guar gum, locust bean gum, or tara gum), xanthan gum, chitosan, pectin, starch, tragacanth, carrageenan, polyvinylpyrrolidone, polyvinyl alcohol, paraffin, petrolatum, silicates, fibroin, or a combination thereof. In still further embodiments, the gelling agent is hyaluronan. In other embodiments, the gelling agent is a combination of hyaluronan and methylcellulose. In yet other embodiments, the gelling agent is a polyoxyethylene-polyoxypropylene block copolymer (e.g., poloxamer (e.g., poloxamer 407 or a combination of poloxamer 407 and poloxamer 188)). In still other embodiments, the gelling agent is fibroin. In some embodiments, the pharmaceutical composition contains at least about 0.5% (w/v) (e.g., at least 0.8% (w/v), at least 1% (w/v), or at least 2% (w/v)) of the gelling agent relative to the liquid solvent. In certain embodiments, the pharmaceutical composition contains about 20% (w/v) or less (e.g., 15% (w/v) or less) of the gelling agent relative to the liquid solvent. In further embodiments, the pharmaceutical composition contains about 2% (w/v) or less of the gelling agent relative to the liquid solvent. In yet further embodiments, the pharmaceutical composition contains about 0.8% (w/v) of the gelling agent relative to the liquid solvent. In still further embodiments, the pharmaceutical composition contains about 1% (w/v) of the gelling agent relative to the liquid solvent.

In particular embodiments, the gelling agent is cross-linked (e.g., ionically cross-linked or covalently cross-linked). In other embodiments, the gelling agent is not cross-linked. In particular embodiments, the pharmaceutical compositions further include a pharmaceutically acceptable liquid solvent (e.g., water).

In yet other embodiments, the concentration of the anti-platinum chemoprotectant agent is at least about 0.05M (e.g., at least about 0.1M, at least about 0.2M, at least about 0.3M, at least about 0.4M, at least about 0.5M, or at least about 1M). In still other embodiments, the concentration of the anti-platinum chemoprotectant agent is about 2.5M or less (e.g., 2.0M or less, 1.5M or less, 1.0M or less, 0.5M or less, about 0.3M or less, or about 0.2M or less). In certain preferred embodiments, the concentration of the anti-platinum chemoprotectant agent is about 0.5M to about 1.5M. In more preferred embodiments, the concentration of the anti-platinum chemoprotectant agent is about 1.0M to about 1.5M.

In some embodiments, the pharmaceutical composition has a pH of 5.0 to 8.5. In certain embodiments, the pharmaceutical composition has a pH of 6.0 to 8.5. In particular embodiments, the pharmaceutical composition has a pH of 6.5 to 8.5.

In further embodiments, the pharmaceutical composition is a pharmaceutical dosage form.

In another aspect, the invention provides a method of preventing or mitigating platinum-induced ototoxicity in a subject by administering to the round window of the subject an effective amount of the pharmaceutical composition (e.g., pharmaceutical dosage form) of the invention. In certain embodiments, the platinum-induced ototoxicity is in the subject receiving a platinum-based antineoplastic agent (e.g., cisplatin, carboplatin, oxaliplatin, nedaplatin, triplatin tetranitrate, phenanthriplatin, picoplatin, or satraplatin).

In some embodiments, the pharmaceutical composition is administered intratympanically or transtympanically. In particular embodiments, the pharmaceutical composition is administered before or after (e.g., within about 24, 12, 11, 10, 9, 8, 7, 6, 5, 4, 3, 2, or 1 hours) the administration of a platinum-based antineoplastic agent. In certain embodiments, the pharmaceutical composition is administered at the same time as the administration of a platinum-based antineoplastic agent. In further embodiments, the pharmaceutical composition is administered by a route different from the platinum-based antineoplastic agent (e.g., the platinum-based antineoplastic agent is administered parenterally (e.g., intratumorally, intramuscularly, or intravenously)). In yet further embodiments, at least 50 µL (preferably, at least 100 µL; more preferably, at least 200 µL) of the pharmaceutical composition are administered to the round window of the subject. In still further embodiments, 1 mL or less of the pharmaceutical composition are administered to the round window of the subject. In other embodiments, the subject is human.

In yet another aspect, the invention provides a method of preparing a pharmaceutical composition (e.g., a pharmaceutical dosage form) of the invention by (i) providing the anti-platinum chemoprotectant agent and the gelling agent, and (ii) mixing the anti-platinum chemoprotectant agent and the gelling agent with the liquid solvent to produce the hypertonic pharmaceutical composition.

In some embodiments, the anti-platinum chemoprotectant agent and the gelling agent are provided as a mixture. In certain embodiments, the anti-platinum chemoprotectant agent and the gelling agent are provided separately, and step (ii) comprises mixing the liquid solvent first with the gelling agent to produce an intermediate mixture and thereafter mixing the intermediate mixture with the anti-platinum chemoprotectant agent. In particular embodiments, the anti-platinum chemoprotectant agent and the gelling agent are provided separately, and step (ii) comprises mixing the liquid solvent first with the anti-platinum chemoprotectant agent to produce an intermediate mixture and thereafter mixing the intermediate mixture with the gelling agent. In further embodiments, the anti-platinum chemoprotectant agent and the gelling agent are provided separately, and step (ii) comprises mixing a portion of the liquid solvent with the anti-platinum chemoprotectant agent to produce a first mixture, mixing another portion of the liquid solvent with the gelling agent to produce a second mixture, and combining the first and second mixtures.

Definitions

The term "about," as used herein, represents a value that is in the range of ±10% of the value that follows the term "about."

The term "alkaline salt," as used herein, represents a sodium or potassium salt of a compound. Alkaline salts may be monobasic or, if the number of acidic moieties (e.g., —COOH, —SO$_3$H, or —P(O)(OH)$_n$ moieties) permits, dibasic or tribasic.

The term "ammonium salt," as used herein, represents an NH$_4^+$ salt of a compound. Ammonium salts may be monobasic or, if the number of acidic moieties (e.g., —COOH, —SO$_3$H, or —P(O)(OH)$_n$ moieties) permits, dibasic or tribasic.

The term "anti-platinum chemoprotectant agent," as used herein, refers to a compound that deactivates platinum-based antineoplastic agents. Without wishing to be bound by theory, an anti-platinum chemoprotectant agent may coordinate to the platinum center of a platinum-based antineoplastic agent, thereby reducing the amount of active platinum centers available for reaction with peptides and/or nucleotides present in a subject. Non-limiting examples of anti-platinum chemoprotectant agents include an alkaline or ammonium thiosulfate salt (e.g., sodium thiosulfate, potassium thiosulfate, or ammonium thiosulfate) or a solvate thereof (e.g., sodium thiosulfate pentahydrate), an alkaline diethyldithiocarbamate salt, amifostine, methionine, N-acetylcysteine, cysteine, 2-aminoethanethiol, glutathione (GSH) or a $C_1$-$C_6$ alkyl ester thereof (e.g., glutathione ethyl ester: γ-Glu-Cys-Gly-OEt) or a salt thereof, lysine or a salt thereof, histidine or a salt thereof, arginine or a salt thereof, ethylene diamine tetraacetic acid or a salt thereof (e.g., an alkaline salt), dimercaprol, dimercaptosuccinic acid or a salt thereof (e.g., an alkaline salt), dimercapto-propane sulfonate salt (e.g., alkaline salt or ammonium salt), penicillamine, α-lipoic acid or a salt thereof (e.g., an alkaline or ammonium salt), or fursultiamine or a salt thereof. The salts of anti-platinum chemoprotectant agents are pharmaceutically acceptable salts.

The term "gelling agent," as used herein, refers to pharmaceutically acceptable excipient known in the art to produce a gel upon mixing with a solvent (e.g., an aqueous solvent). Non-limiting examples of gelling agents include hyaluronan, a polyoxyethylene-polyoxypropylene block copolymer (e.g., a poloxamer), poly(lactic-co-glycolic) acid, polylactic acid, polycaprolactone, alginic acid or a salt thereof, polyethylene glycol, a cellulose, a cellulose ether, a carbomer (e.g., Carbopol®), agar-agar, gelatin, glucomannan, galactomannan (e.g., guar gum, locust bean gum, or tara gum), xanthan gum, chitosan, pectin, starch, tragacanth, carrageenan, polyvinylpyrrolidone, polyvinyl alcohol, paraffin, petrolatum, silicates, fibroin, and combinations thereof.

The term "hypertonic," as used herein in reference to pharmaceutical compositions, represents a pharmaceutical composition having a calculated osmolarity of 300 mOsm/L to 7,000 mOsm/L (e.g., 300 mOsm/L to 2,500 mOsm/L), which corresponds to 300 mmol to 7,000 mmol (e.g., 300 mOsm/L to 2,500 mmol) of ions and/or neutral molecules produced by dissolution of platinum-deactivating agent and any ionic, non-polymeric excipients in 1 L of solvent having calculated osmolarity of 0 mOsm/L. For the purpose of the present disclosure, the calculated osmolarity does not include ions and/or neutral molecules produced from polymeric excipients (e.g., from a gelling agent). For the purpose of this disclosure, polymeric excipients (e.g., a gelling agents) are deemed as not contributing to the calculated osmolarity of the compositions disclosed herein.

The term "intratympanic," as used herein in reference to a route of administration, means delivery to the round window by injection or infusion through an ear canal with a temporarily removed or lifted tympanic membrane or through a port created through an auditory bulla into the middle ear of a subject.

The term "pharmaceutical composition," as used herein, represents a composition formulated with a pharmaceutically acceptable excipient, and manufactured or sold with the approval of a governmental regulatory agency as part of a therapeutic regimen for the treatment of disease in a mammal.

The term "pharmaceutical dosage form," as used herein, represents those pharmaceutical compositions intended for administration to a subject as is without further modification (e.g., without dilution with, suspension in, or dissolution in a liquid solvent).

The term "pharmaceutically acceptable excipient," as used herein, refers to any ingredient other than the anti-platinum chemoprotectant agents and gelling agents described herein (e.g., a vehicle capable of suspending or dissolving the active compound) and having the properties of being substantially non-toxic and substantially non-inflammatory in a patient. Excipients may include, e.g., antioxidants, disintegrants, dyes (colors), emollients, emulsifiers, fillers (diluents), flavors, fragrances, preservatives, printing inks, sorbents, suspending or dispersing agents, sweeteners, liquid solvents, and buffering agents.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "pharmaceutically acceptable solvate" as used herein means a compound as described herein wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, tri-, tetra-, and penta-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When the solvate is water-based, the solvate is referred to as a hydrate.

The term "platinum-based antineoplastic agent," as used herein, represents a coordination compound of Pt(II) or Pt(IV). Platinum-based antineoplastic agents are known in the art as platins. Typically, platinum-based antineoplastic agents include at least two coordination sites at the platinum center that are occupied by nitrogenous spectator ligand(s). The nitrogenous spectator ligands are monodentate or bidentate ligands, in which the donor atom is an spa- or $sp^2$-hybridized nitrogen atom within the ligand. Non-limiting examples of nitrogenous spectator ligands are ammonia, 1,2-cyclohexanediamine, a picoline, phenanthrin, or 1,6-hexanediamine. Non-limiting examples of platinum-based antineoplastic agents include cisplatin, carboplatin, oxaliplatin, nedaplatin, triplatin tetranitrate, phenanthriplatin, picoplatin, and satraplatin.

The term "subject," as used herein, refers to an animal (e.g., a mammal, e.g., a human). A subject to be treated according to the methods described herein may be one who is being treated with a therapeutic regimen including a platinum-based antineoplastic agent (e.g., for the treatment of a benign tumor, malignant tumor, or cancer). The patient may have been diagnosed with a benign tumor, malignant tumor, or cancer by any method or technique known in the art. One skilled in the art will understand that a subject to be treated according to the invention may have been subjected to standard tests or may have been identified, without examination, as one at high risk due to receiving a therapeutic regimen including a platinum-based antineoplastic agent.

The term "substantially neutral," used herein, refers to a pH level of 5.5 to about 8.5, as measured at 20° C.

The term "tonicity agent," as used herein, refers to a class of pharmaceutically acceptable excipients that are used to control osmolarity of pharmaceutical compositions. Non-limiting examples of a tonicity agent include substantially neutral buffering agents (e.g., phosphate buffered saline, tris buffer, or artificial perilymph), dextrose, mannitol, glycerin, potassium chloride, and sodium chloride (e.g., as a hypertonic, isotonic, or hypotonic saline). Artificial perilymph is an aqueous solution containing NaCl (120-130 mM), KCl (3.5 mM), $CaCl_2$ (1.3-1.5 mM), $MgCl_2$ (1.2 mM), glucose (5.0-11 mM), and buffering agents (e.g., $NaHCO_3$ (25 mM) and $NaH_2PO_4$ (0.75 mM), or HEPES (20 mM) and NaOH (adjusted to pH of about 7.5)).

The term "transtympanic," as used herein in reference to a route of administration, means delivery to the round window by injection or infusion across tympanic membrane. A transtympanic injection may be performed directly through the tympanic membrane or through a tube embedded in the tympanic membrane (e.g., through a tympanostomy tube or grommet).

DETAILED DESCRIPTION

Figure 1A:
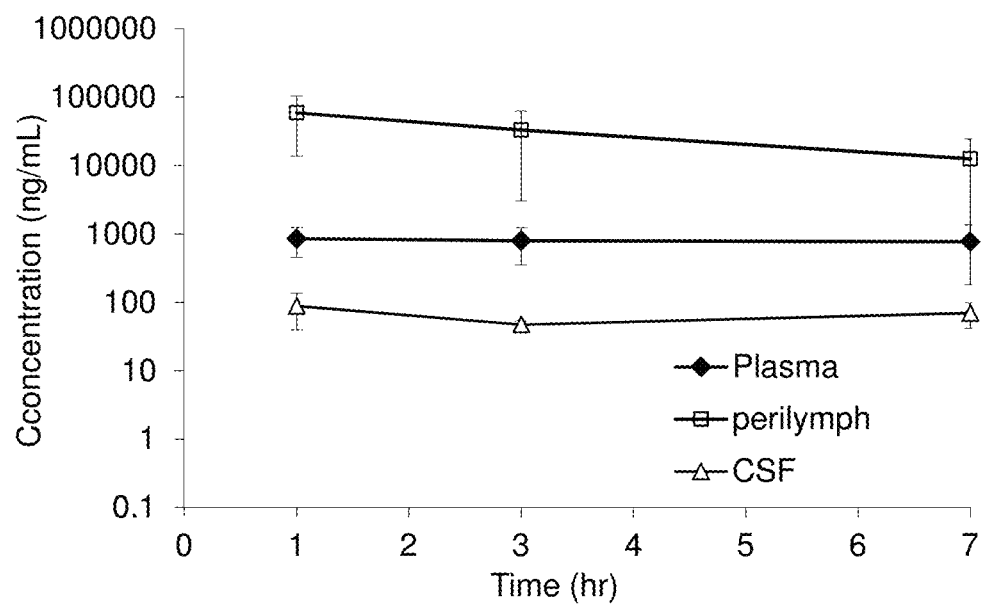
FIG. 1A is a chart showing the changes in thiosulfate concentrations over time in plasma, perilymph, and cerebrospinal fluid in guinea pigs administered a gel containing 0.1M sodium thiosulfate and 20% (w/v) poloxamer 407.
Figure 1B:
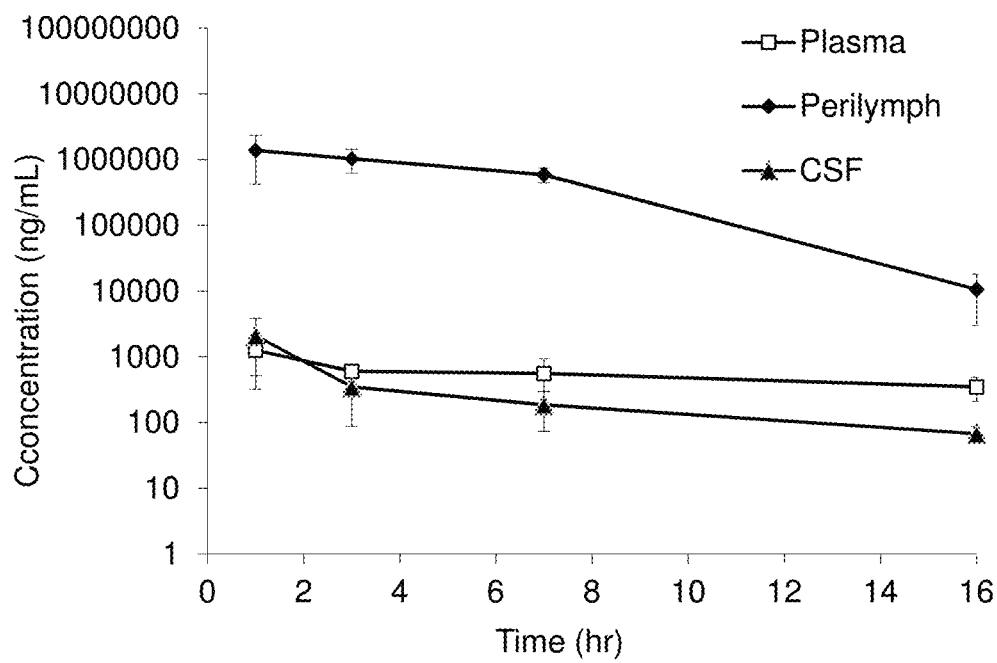
FIG. 1B is a chart showing the changes in thiosulfate concentrations over time in plasma, perilymph, and cerebrospinal fluid in guinea pigs administered a gel containing 0.5M sodium thiosulfate and 1% (w/v) hyaluronan.
Figure 2A:
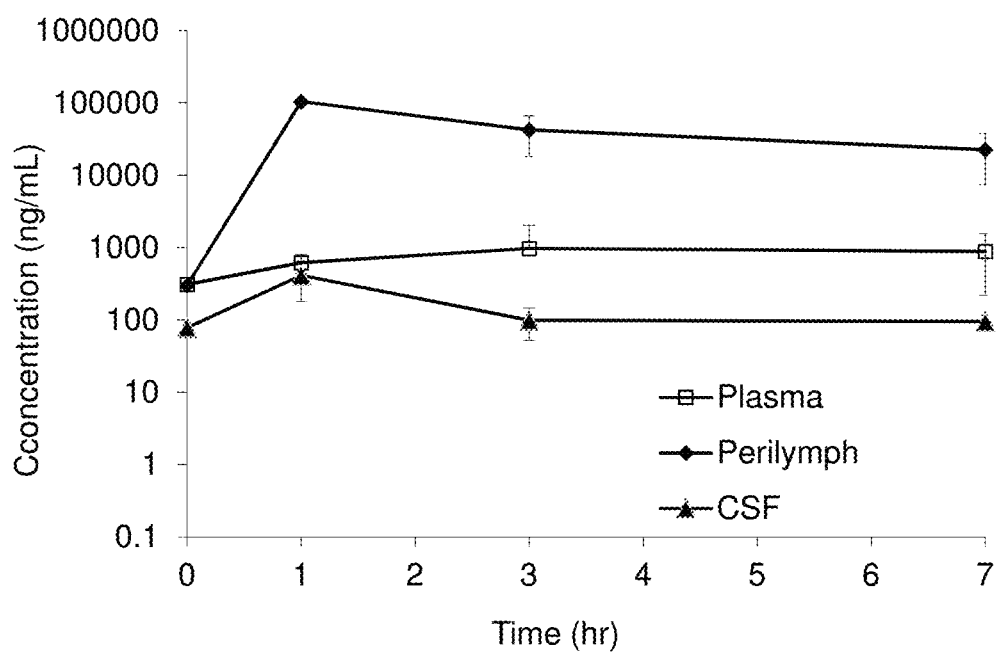
FIG. 2A is a chart showing the changes in thiosulfate concentrations over time in plasma, perilymph, and cerebrospinal fluid in guinea pigs administered a gel containing 0.1M sodium thiosulfate and 2% (w/v) hyaluronan.
Figure 2B:
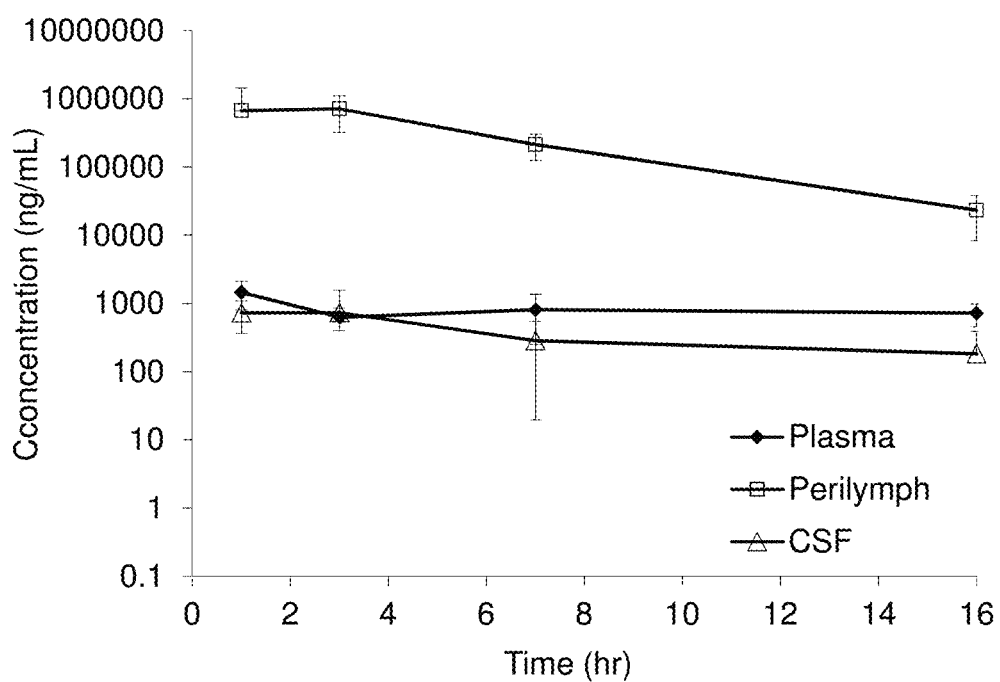
FIG. 2B is a chart showing the changes in thiosulfate concentrations over time in plasma, perilymph, and cerebrospinal fluid in guinea pigs administered a gel containing 0.5M sodium thiosulfate and 2% (w/v) hyaluronan.

In general, the invention provides pharmaceutical compositions containing anti-platinum chemoprotectant agents. The pharmaceutical compositions of the invention may be used in the treatment of platinum-induced ototoxicity in a subject receiving a platinum-based antineoplastic agent (e.g., a subject having a tumor or cancer). Non-limiting examples of the platinum-based antineoplastic agents include cisplatin, carboplatin, oxaliplatin, nedaplatin, triplatin tetranitrate, phenanthriplatin, picoplatin, and satraplatin.

The pharmaceutical compositions of the invention may prevent or mitigate hearing loss in a subject receiving a platinum-based antineoplastic agent, as measured by at least 50% (e.g., at least 60%, at least 70%, or at least 80%) reduction in the sound pressure level threshold elevation in the subject at a frequency 8 kHz or higher (e.g., between 8 kHz and 20 kHz) relative to a reference subject that receives the same platinum-based antineoplastic agent regimen but does not receive the anti-platinum chemoprotectant agent.

The pharmaceutical compositions of the invention are hypertonic. Without wishing to be bound by theory, the higher tonicity of the pharmaceutical compositions of the invention is believed to improve the bioavailability of anti-platinum chemoprotectant agents at the round window of a subject, relative to compositions with lower tonicity (e.g., hypotonic or isotonic). The bioavailability is typically measured as $AUC_{inf}$ for an anti-platinum chemoprotectant agent following its administration to an animal (e.g., a mammal). The calculated osmolarity of the pharmaceutical composition of the invention (e.g., pharmaceutical dosage form) may be, e.g., at least 400 mOsm/L (e.g., at least 500 mOsm/L, at least 600 mOsm/L, at least 700 mOsm/L, at least 800 mOsm/L, at least 900 mOsm/L, at least 1,000 mOsm/L, at least 1,500 mOsm/L, at least 2,000 mOsm/L, at least 2,500 mOsm/L, or at least 3,000 mOsm/L), and/or 5,000 mOsm/L or less (e.g., 4,000 mOsm/L or less, 3,000 mOsm/L or less, 2,000 mOsm/L or less, 1,900 mOsm/L or less, 1,800 mOsm/L or less, 1,700 mOsm/L or less, 1,600 mOsm/L or less, or 1,500 mOsm/L or less). The calculated osmolarity of the pharmaceutical composition of the invention (e.g., pharmaceutical dosage form) may be, e.g., 1,500-4,500 mOsm/L. The calculated osmolarity of the pharmaceutical composition of the invention (e.g., pharmaceutical dosage forms) may be, e.g., 3,000-4,500 mOsm/L. The measured osmolality of the pharmaceutical composition of the invention (e.g., pharmaceutical dosage form) may be, e.g., at least 0.3 Osm/kg (e.g., at least 0.5 Osm/kg, at least 0.6 Osm/kg, at least 0.7 Osm/kg, at least 0.8 Osm/kg, at least 0.9 Osm/kg, at least 1.0 Osm/kg, at least 1.2 Osm/kg, at least 1.4 Osm/kg, or at least 1.8 Osm/kg). The measured osmolality of the pharmaceutical composition of the invention (e.g., pharmaceutical dosage form) may be, e.g., 2.5 Osm/kg or less (e.g., 2.1 Osm/kg or less). The measured osmolality of the pharmaceutical composition of the invention (e.g., pharmaceutical dosage form) may be, e.g., 0.3-2.5 Osm/kg (e.g., 0.5-2.5 Osm/kg, 0.6-2.5 Osm/kg, 0.7-2.5 Osm/kg, 0.8-2.5 Osm/kg, 0.9-2.5 Osm/kg, 1.0-2.5 Osm/kg, 1.2-2.5 Osm/kg, 1.4-2.5 Osm/kg, 1.8-2.5 Osm/kg, 0.5-2.1 Osm/kg, 0.6-2.1 Osm/kg, 0.7-2.1 Osm/kg, 0.8-2.1 Osm/kg, 0.9-2.1 Osm/kg, 1.0-2.1 Osm/kg, 1.2-2.1 Osm/kg, 1.4-2.1 Osm/kg, or 1.8-2.1 Osm/kg). "Calculated osmolarity" refers to the number of mmoles of ions and/or neutral molecules produced by dissolution of one or more compounds in 1 L of DI or distilled water; calculated osmolarity does not include ions and/or neutral molecules produced from polymeric excipients (e.g., from a gelling agent). "Measured osmolality" refers to the osmolality of a composition, as measured using an osmometer (typically, a membrane osmometer).

An anti-platinum chemoprotectant agent may be, e.g., the sole compound contributing to osmolarity of a pharmaceutical composition of the invention. Alternatively, higher osmolalities than those afforded by the desired concentration of an anti-platinum chemoprotectant agent may be achieved, e.g., through the use of tonicity agents. A tonicity agent may be present in a hypertonic, isotonic, or hypotonic excipient (e.g., a hypotonic liquid solvent). Non-limiting examples of tonicity agents include substantially neutral buffering agents (e.g., phosphate buffered saline, tris buffer, or artificial perilymph), dextrose, mannitol, glycerin, potassium chloride, and sodium chloride (e.g., as a hypertonic, isotonic, or hypotonic saline).

Anti-Platinum Chemoprotectant Agents

Pharmaceutical compositions of the invention contain an anti-platinum chemoprotectant agent. Without wishing to be bound by theory, anti-platinum chemoprotectant agents are believed to reduce or eliminate the toxicity of platin-based antineoplastic agents by competitively ligating and substantially coordinatively saturating the platinum centers present in the platinum-based antineoplastic agents. The concentration of an anti-platinum chemoprotectant agent in a pharmaceutical composition (e.g., a pharmaceutical dosage form) of the invention may be, e.g., at least about 0.05M (e.g., at least about 0.1M, at least about 0.2M, at least about 0.3M, at least about 0.4M, at least about 0.5M, or at least about 1M). The concentration of an anti-platinum chemoprotectant agent in a pharmaceutical composition (e.g., a pharmaceutical dosage form) of the invention may be, e.g., about 2.5M or less (e.g., 2.0M or less, 1.5M or less, 1.0M or less, 0.5M or less, about 0.3M or less, or about 0.2M or less). Non-limiting examples of the concentrations of an anti-platinum chemoprotectant agent in a pharmaceutical composition (e.g., a pharmaceutical dosage form) of the invention may be, e.g., about 0.05M to about 1.5M, about 0.05M to about 0.5M, about 0.05M to about 0.2M, about 0.05M to about 0.1M, about 0.1M to about 1.5M, about 0.1M to about 0.5M, about 0.1M to about 0.2M, about 0.2M to about 1.5M, about 0.2M to about 0.5M, about 0.5M to about 1.5M, 0.05M to about 1.0M, about 0.05M to about 0.5M, about 0.05M to about 0.2M, about 0.05M to about 0.1M, about 0.1M to about 1.0M, about 0.1M to about 0.5M, about 0.1M to about 0.2M, about 0.2M to about 1.0M, about 0.2M to about 0.5M, or about 0.5M to about 1.0M, or about 1.0M to about 1.5M. Preferably, the concentration of an anti-platinum chemoprotectant agent in a pharmaceutical composition (e.g., a pharmaceutical dosage form) of the invention is about 1.0M to about 1.5M.

Anti-platinum chemoprotectant agents are known in the art. Non-limiting examples of anti-platinum chemoprotectant agents include an alkaline or ammonium thiosulfate salt (e.g., sodium thiosulfate, potassium thiosulfate, or ammonium thiosulfate) or a solvate thereof (e.g., sodium thiosulfate pentahydrate), an alkaline diethyldithiocarbamate salt, amifostine, methionine, N-acetylcysteine, cysteine, 2-aminoethanethiol, glutathione (GSH) or a $C_1$-$C_6$ alkyl ester thereof (e.g., glutathione ethyl ester: γ-Glu-Cys-Gly-OEt) or a salt thereof, lysine or a salt thereof, histidine or a salt thereof, arginine or a salt thereof, ethylene diamine tetraacetic acid or a salt thereof (e.g., an alkaline salt), dimercaprol, dimercaptosuccinic acid or a salt thereof (e.g., an alkaline salt), dimercapto-propane sulfonate salt (e.g., alkaline salt or ammonium salt), penicillamine, α-lipoic acid or a salt thereof (e.g., an alkaline or ammonium salt), or fursultiamine or a salt thereof. Preferably, the anti-platinum chemoprotectant agent is an alkaline or ammonium thiosulfate salt. More preferably, the anti-platinum chemoprotectant agent is sodium thiosulfate.

Gelling Agents

Pharmaceutical compositions of the invention include a gelling agent. Gelling agents may be used to increase the viscosity of the pharmaceutical composition, thereby improving the retention of the pharmaceutical composition at the targeted site. Pharmaceutical compositions (e.g., pharmaceutical dosage forms) of the invention may contain, e.g., about 0.1% to about 25% (w/v) (e.g., about 0.1% to about 20% (w/v), about 0.1% to about 10% (w/v), about 0.1% to about 2% (w/v), about 0.5% to about 25% (w/v), about 0.5% to about 20% (w/v), about 0.5% to about 10% (w/v), about 0.5% to about 2% (w/v), about 1% to about 20% (w/v), about 1% to about 10% (w/v), about 1% to about 2% (w/v), about 5% to about 20% (w/v), about 5% to about 10% (w/v), or about 7% to about 10% (w/v)) of a gelling agent relative to solvent. Preferably, pharmaceutical compositions (e.g., pharmaceutical dosage forms) of the invention may contain, e.g., about 0.5% to about 25% (w/v) (e.g., about 0.5% to about 20% (w/v), about 0.5% to about 10% (w/v), about 0.5% to about 2% (w/v), about 1% to about 20% (w/v), about 1% to about 10% (w/v), about 1% to about 2% (w/v), about 5% to about 20% (w/v), about 5% to about 10% (w/v), or about 7% to about 10% (w/v)) of a gelling agent relative to solvent.

Gelling agents that may be used in the pharmaceutical compositions of the invention are known in the art. Non-limiting examples of gelling agents include hyaluronan, a polyoxyethylene-polyoxypropylene block copolymer (e.g., a poloxamer), poly(lactic-co-glycolic) acid, polylactic acid, polycaprolactone, alginic acid or a salt thereof, polyethylene glycol, a cellulose, a cellulose ether, a carbomer (e.g., Carbopol®), agar-agar, gelatin, glucomannan, galactomannan (e.g., guar gum, locust bean gum, or tara gum), xanthan gum, chitosan, pectin, starch, tragacanth, carrageenan, polyvinylpyrrolidone, polyvinyl alcohol, paraffin, petrolatum, silicates, fibroin, and combinations thereof. The gelling agents described herein are known in the art. Preferably, the gelling agent is hyaluronan.

A pharmaceutical composition of the invention may contain, e.g., about 0.5% to about 2% (w/v) (e.g., about 1% to about 2% (w/v)) of hyaluronan relative to solvent. A pharmaceutical composition of the invention may contain, e.g., about 5% to about 10% (w/v) (e.g., about 6% to about 8% (w/v)) of methylcellulose relative to solvent. A pharmaceutical composition of the invention may contain, e.g., hyaluronan and methylcellulose as a gelling agent (e.g., about 0.5% to about 2% (w/v) of hyaluronan and about 5% to about 10% (w/v) of methylcellulose relative to solvent). A pharmaceutical composition of the invention may contain, e.g., a polyoxyethylene-polyoxypropylene block copolymer (e.g., poloxamer) as a gelling agent. A pharmaceutical composition of the invention may contain, e.g., about 1% to about 20% (w/v) (e.g., about 1% to about 15% (w/v), about 1% to about 10% (w/v), about 5% to about 20% (w/v), about 5% to about 15% (w/v), about 5% to about 10% (w/v), about 10% to about 20% (w/v), or about 10% to about 15% (w/v)) of a polyoxyethylene-polyoxypropylene block copolymer (e.g., poloxamer) relative to solvent. The poloxamer may be poloxamer 407, poloxamer 188, or a combination thereof. A pharmaceutical composition of the invention may contain, e.g., about 0.5% (w/v) to about 20% (w/v) of fibroin as a gelling agent relative to solvent.

Hyaluronan is a hyaluronic acid or a salt thereof (e.g., sodium hyaluronate). Hyaluronans are known in the art and are typically isolated from various bacteria (e.g., *Streptococcus zooepidemicus*, *Streptococcus equi*, or *Streptococcus pyrogenes*) or other sources, e.g., bovine vitreous humor or rooster combs. The weight-averaged molecular weight ($M_w$) of hyaluronan is typically about 50 kDa to about 10 MDa. Preferably, $M_w$ of a hyaluronan (e.g., sodium hyaluronate) is about 500 kDa to 6 MDa (e.g., about 500 kDa to about 750 kDa, about 600 kDa to about 1.1 MDa, about 750 kDa to about 1 MDa, about 1 MDa to about 1.25 MDa, about 1.25 to about 1.5 MDa, about 1.5 MDa to about 1.75 MDa, about 1.75 MDa to about 2 MDa, about 2 MDa to about 2.2 MDa, about 2 MDa to about 2.4 MDa). More preferably, the $M_w$ of a hyaluronan (e.g., sodium hyaluronate) is about 620 kDa to about 1.2 MDa or about 1.2 MDa to about 1.9 MDa. Other preferred molecular weight ranges for a hyaluronan include, e.g., about 600 kDa to about 1.2 MDa.

Polyoxyethylene-polyoxypropylene block copolymers are known in the art. A non-limiting example of polyoxyethylene-polyoxypropylene block copolymers is a poloxamer, in which a single polyoxypropylene block is flanked by two polyoxyethylene blocks. Poloxamers are commercially available under various trade names, e.g., Synperonic®, Pluronic®, Kolliphor®, and Lutrol®. A pharmaceutical composition of the invention may contain, e.g., a polyoxyethylene-polyoxypropylene block copolymer (e.g., a poloxamer) includes a polyoxypropylene block with a number average molecular weight (Mr) of, e.g., about 1,100 g/mol to about 17,400 g/mol (e.g., about 2,090 g/mol to about 2,360 g/mol, about 7,680 g/mol to about 9,510 g/mol, 6,830 g/mol to about 8,830 g/mol, about 9,840 g/mol to about 14,600 g/mol, or about 12,700 g/mol to about 17,400 g/mol). A polyoxyethylene-polyoxypropylene block copolymer (e.g., a poloxamer) may include a polyoxypropylene block with a number average molecular weight ($M_n$) of about 1,100 g/mol to about 4,000 g/mol and a calculated polyoxyethylene content of about 30% to about 85% (w/w). Preferably, a polyoxyethylene-polyoxypropylene block copolymer (e.g., a poloxamer) may include a polyoxypropylene block with a calculated molecular weight of, e.g., about 1,800 g/mol to about 4,000 g/mol. Preferably, the calculated polyoxyethylene content a polyoxyethylene-polyoxypropylene block copolymer (e.g., a poloxamer) may be, e.g., about 70% to about 80% (w/w). Preferably, a polyoxyethylene-polyoxypropylene block copolymer (e.g., a poloxamer) may have a number average molecular weight of, e.g., about 7,680 g/mol to about 14,600 g/mol. Non-limiting examples of poloxamers are poloxamer 407 and poloxamer 188.

Celluloses and cellulose ethers are known in the art. Celluloses and cellulose ethers are commercially available under various tradenames, e.g., Avicel®, Methocel™, Natrosol®, and Tylose®. Non-limiting examples of cellulose ethers include methylcellulose, carboxymethylcellulose, ethylcellulose, hydroxyethylcellulose, methyl hydroxyethylcellulose, hydroxypropyl methylcellulose, or hydroxypropylcellulose. A cellulose ether (e.g., methylcellulose) may have a number average molecular weight (Mr) of, e.g., about 5 kDa to about 300 kDa. Methyl-substituted celluloses (e.g., methylcellulose, hydroxypropyl methyl cellulose, or methyl hydroxyethylcellulose) may have methyl content of, e.g., 19% to 35% (e.g., 19% to 30%).

Fibroin is a protein present in silk created by numerous insects. Fibroins are known in the art and are commercially available from various vendors, e.g., Jiangsu SOHO International Group; Simatech, Suzhou, China; Xi'an Lyphar Biotech, Ltd.; Xi'an Rongsheng Biotechnology; Mulberry Farms, Treenway Silks, Sharda Group, Maniar Enterprises, and Wild Fibres. The molecular weight of silk fibroin is typically about 10 kDa to about 500 kDa. Fibroins are described in WO 2017/139684, the disclosure of which is incorporated herein by reference.

Cross-Linked Gelling Agents

Pharmaceutical compositions of the invention may contain non-cross-linked or cross-linked gelling agents. Gelling agents may be cross-linked using cross-linking agents known in the art. Preferably, the cross-linked gelling agent is covalently crosslinked. Pharmaceutical compositions (e.g., pharmaceutical dosage forms) including cross-linked gelling agents may be used to control the release profile of an anti-platinum chemoprotectant agent. For example, the release of an anti-platinum chemoprotectant agent from a pharmaceutical composition (e.g., a pharmaceutical dosage form) containing a cross-linked gelling agent may be extended release relative to a reference composition that differs from the pharmaceutical composition only by the lack of cross-linking in the gelling agent in the reference composition. The extension of the release of an anti-platinum chemoprotectant agent may be assessed by comparing $T_{max}$ values for the pharmaceutical composition and the reference composition.

Certain gelling agents, e.g., those having carboxylate moieties (e.g., hyaluronan, alginic acid, and carboxymethylcellulose), can be cross-linked ionically using ionic cross-linking agents (e.g., a multivalent metal ion, e.g., $Mg^{2+}$, $Ca^{2+}$, or $Al^{3+}$). Techniques for ionic cross-linking of gelling agents are known in the art (see, e.g., U.S. Pat. Nos. 6,497,902 and 7,790,699, the disclosures of which are incorporated herein by reference). Typically, gelling agents can be ionically cross-linked in an aqueous solution using multivalent metal ions, e.g., $Mg^{2+}$, $Ca^{2+}$, or $Al^{3+}$, as ionic cross-linking agents. Without wishing to be bound by theory, the metal ions are believed to coordinate to different molecules of the gelling agent (e.g., to pendant carboxylates residing on different molecules of the gelling agent), thereby forming a linkage between these different molecules of the gelling agent.

Certain gelling agents having reactive functional groups, e.g., —OH, —COOH, or —NH₂, may be covalently cross-linked. Techniques for covalent cross-linking of gelling agents are known in the art (see, e.g., Khunmanee et al., *J. Tissue Eng.*, 8: 2041731417726464, 2017, the disclosure of which is incorporated herein by reference). Non-limiting examples of covalent cross-linking agents include: 1,4-butanediol diglycidyl ether (BDDE), divinyl sulfone, glutaraldehyde, cyanogen bromide, octeylsuccinic anhydride, acid chlorides, diisocyanates, methacrylic anhydride, boric acid, and sodium periodate/adipic acid dihydrazide.

Other Excipients

Pharmaceutical compositions of the invention may contain pharmaceutically excipients other than gelling agents. For example, pharmaceutical compositions of the invention may contain, e.g., liquid solvents, tonicity agents, buffering agents, and/or coloring agents. Certain excipients may perform multiple roles. For example, a liquid solvent in addition to its function as a carrier may be used as a tonicity agent and/or buffering agent. Such solvents are known in the art, e.g., salines (e.g., hypertonic saline, hypotonic saline, isotonic saline, or phosphate-buffered saline) and artificial perilymph.

Liquid solvents may be used in pharmaceutical compositions (e.g., pharmaceutical dosage forms) of the invention as a vehicle. Liquid solvents are known in the art. Non-limiting examples of liquid solvents include water, salines (e.g., hypertonic saline, hypotonic saline, isotonic saline, or phosphate-buffered saline), artificial perilymph, and tris buffer. Artificial perilymph is an aqueous solution containing NaCl (120-130 mM), KCl (3.5 mM), $CaCl_2$ (1.3-1.5 mM), $MgCl_2$ (1.2 mM), glucose (5.0-11 mM), and buffering agents (e.g., $NaHCO_3$ (25 mM) and $NaH_2PO_4$ (0.75 mM), or HEPES (20 mM) and NaOH (adjusted to pH of about 7.5)). Tonicity agents may be included in pharmaceutical compositions (e.g., pharmaceutical dosage forms) of the invention to increase osmolarity relative to that which is afforded by an anti-platinum chemoprotectant agent. Tonicity agents are known in the art. Non-limiting examples of tonicity agents include substantially neutral buffering agents (e.g., phosphate buffered saline, tris buffer, or artificial perilymph), dextrose, mannitol, glycerin, potassium chloride, and sodium chloride (e.g., as a hypertonic, isotonic, or hypotonic saline). Pharmaceutical compositions (e.g., pharmaceutical dosage forms) of the invention include sufficient amount of tonicity agents to provide for administration to a subject a hypertonic pharmaceutical dosage form (e.g., a pharmaceutical dosage form having a calculated osmolarity of at least 400 mOsm/L (e.g., at least 500 mOsm/L, at least 600 mOsm/L, or at least 700 mOsm/L), and/or 2,500 mOsm/L or less (e.g., 2,000 mOsm/L, 1,900 mOsm/L or less, 1,800 mOsm/L or less, 1,700 mOsm/L or less, 1,600 mOsm/L or less, or 1,500 mOsm/L or less)). For example, the targeted concentration of a tonicity agent in a pharmaceutical composition (e.g., pharmaceutical dosage form) of the invention can be determined, e.g., by (i) subtracting the calculated osmolarity contributions of an anti-platinum chemoprotectant agent and other non-polymeric excipients from the total targeted calculated osmolarity to obtain the targeted calculated osmolarity contribution from the tonicity agent, and (ii) determining the concentration of the tonicity agent by dividing the targeted calculated osmolarity contribution from the tonicity agent by the number of ions and/or molecules produced upon dissolution of the tonicity agent in a liquid solvent. An appropriate amount of the tonicity agent thus can be included in the pharmaceutical composition (e.g., pharmaceutical dosage form) of the invention.

Buffering agents may be used to adjust the pH of a pharmaceutical composition (e.g., a pharmaceutical dosage form) of the invention a substantially neutral pH level. Buffering agents are known in the art. Non-limiting examples of buffering agents include, e.g., phosphate buffers and Good's buffers (e.g., tris, MES, MOPS, TES, HEPES, HEPPS, tricine, and bicine). In addition to the pH control, buffering agents may be used to control osmolarity of the pharmaceutical composition (e.g., pharmaceutical dosage form) of the invention.

Methods of Use

Pharmaceutical compositions (e.g., pharmaceutical dosage forms) of the invention may exhibit otoprotective properties against platinum-based antineoplastic agents and may be used in a method of preventing or mitigating platinum-induced ototoxicity in subjects in need thereof. The method includes administration of a pharmaceutical composition of the invention to a round window of the subject. The subject may be undergoing therapy with a platinum-based antineoplastic agent (e.g., cisplatin, carboplatin, oxaliplatin, nedaplatin, triplatin tetranitrate, phenanthriplatin, picoplatin, or satraplatin).

A pharmaceutical composition of the invention may be administered to a subject, e.g., before or after the administration of a platinum-based antineoplastic agent to the subject. Alternatively, a pharmaceutical composition of the invention may be administered, e.g., at the same time as the administration of a platinum-based antineoplastic agent. A pharmaceutical composition of the invention may be administered, e.g., within 1 hour of the administration of a platinum-based antineoplastic agent (e.g., within 15 min, 30 min, or 1 hour before or after). Alternatively, a pharmaceutical composition of the invention may be administered, e.g., within 24 hours of a platinum-based antineoplastic agent (e.g., within 1, 2, 3, 4, 5, 6, 7, 8, 9, 10, 11, 12, or 24 hours before or after). A pharmaceutical composition of the invention may be administered without coordination with the administration of a platinum-based antineoplastic agent. Instead, for the period of time during which a subject is receiving chemotherapy including a platinum-based antineoplastic agent, a pharmaceutical composition of the invention may be administered once or twice daily, every other day, twice a week, or weekly.

In some embodiments, at least 50 µL (preferably, at least 100 µL; more preferably, at least 200 µL) of the pharmaceutical composition are administered to the round window of the subject. In particular embodiments, 1 mL or less (e.g., 0.8 mL or less or 0.5 mL or less) of the pharmaceutical composition are administered to the round window of the subject. In certain embodiments, 100 µL to 1 mL (e.g., 200 µL to 1 mL, 100 µL to 0.8 mL, 200 µL to 0.8 mL, 100 µL to 0.5 mL, 200 µL to 0.5 mL, 0.5 mL to 1.0 mL, 0.5 mL to 0.8 mL, or 0.8 mL to 1.0 mL) of the pharmaceutical composition are administered to the round window of the subject.

Typically, the pharmaceutical composition of the invention may be administered by a route different from the platinum-based antineoplastic agent. The methods of the invention may utilize a local route of administration, for example, the pharmaceutical composition of the invention may be administered intratympanically or transtympanically. Transtympanic administration may include injection or infusion of an effective amount of the pharmaceutical composition of the invention through the tympanic membrane into the tympanic cavity, thereby providing the anti-platinum chemoprotectant agent to the round window.

Methods of Preparation

A pharmaceutical composition (e.g., a pharmaceutical dosage form) of the invention may be prepared from an anti-platinum chemoprotectant agent, a gelling agent, and a liquid solvent. A method of preparing a pharmaceutical composition (e.g., a pharmaceutical dosage form) of the invention includes (i) providing the anti-platinum chemoprotectant agent and the gelling agent, and (ii) mixing the anti-platinum chemoprotectant agent and the gelling agent with the liquid solvent to produce the pharmaceutical composition.

The anti-platinum chemoprotectant agent and the gelling agent may be provided, e.g., as a mixture or as separate ingredients. When the anti-platinum chemoprotectant agent and the gelling agent are provided separately, the step (ii) may include, e.g.:

(a) mixing the liquid solvent first with the gelling agent to produce an intermediate mixture and thereafter mixing the intermediate mixture with the anti-platinum chemoprotectant agent;

(b) mixing the liquid solvent first with the anti-platinum chemoprotectant agent to produce an intermediate mixture and thereafter mixing the intermediate mixture with the gelling agent; or (c) mixing a portion of the liquid solvent with the anti-platinum chemoprotectant agent to produce a first mixture, mixing another portion of the liquid solvent with the gelling agent to produce a second mixture, and combining the first and second mixtures.

The following examples are meant to illustrate the invention. They are not meant to limit the invention in any way.

EXAMPLES

Example 1. Formulations

Poloxamer 407 Gel 1 (0.1M STS, 20% (w/v) Poloxamer 407)

Sodium thiosulfate pentahydrate (106.07 mg) was dissolved in sterile, distilled water (4.274 mL) in a sterile vial to produce a clear solution. Poloxamer 407 (855 mg; purified, non-ionic, Sigma-Aldrich) was added into the solution, and the resulting mixture was stirred for 15-20 min at 4° C. Evans blue (4.27 mg) was added into the vial and stirred for 10 mins at 4° C. (ice/water bath).

Poloxamer 407 Gel 2 (0.5M STS, 16% (w/v) Poloxamer 407)

Poloxamer 407 gel 2 was prepared according to the procedure described for Poloxamer 407 gel 1 with the exception that the amount of sodium thiosulfate pentahydrate was adjusted to provide a 0.5M concentration of sodium thiosulfate, and the amount of poloxamer 407 was adjusted to provide a 16% (w/v) concentration of poloxamer 407.

Preparation of Poloxamer 407 gels with 0.6M-0.8M STS, 16% (w/v) poloxamer 407 led to the observation of precipitation without gel formation.

Hyaluronan Gel 1 (0.5M STS, 1% (w/v) Hyaluronan)

Sodium thiosulfate pentahydrate (619.75 mg) was dissolved in sterile, distilled water (5 mL) in a sterile vial to produce a clear solution. Hyaluronan (50.30 mg; Pharma Grade 80, Kikkoman Biochemifa company; 0.6-1.2 mDa) was added to the solution, and the resulting mixture was stirred for 8-10 min at 4° C. The resulting solution was filtered through 0.22 μm Millex-GV sterile filter.

Hyaluronan Gel 2 (0.1M STS, 2% (w/v) Hyaluronan)

Sodium thiosulfate pentahydrate (124.87 mg) was dissolved in sterile, distilled water (3.031 mL). Methylcellulose (351.01 mg; Methocel® A15 Premium LV, Dow Chemical Company) was dissolved in sterile, distilled water (2.0 mL), and the resulting solution was mixed with the sodium thiosulfate solution. Hyaluronan (100.10 mg; Pharma Grade 80, Kikkoman Biochemifa company; 0.6-1.2 mDa) was added to the resulting mixture and mixed at 4° C. for 10-15 min.

Hyaluronan Gel 3 (0.5M STS, 2% (w/v) Hyaluronan)

Sodium thiosulfate pentahydrate (620.35 mg) was dissolved in sterile, distilled water (3 mL). Methylcellulose (350.23 mg; Methocel® A15 Premium LV, Dow Chemical Company) was dissolved in sterile, distilled water (2.0 mL), and the resulting solution was mixed with the sodium thiosulfate solution. Hyaluronan (100.65 mg; Pharma Grade 80, Kikkoman Biochemifa company; 0.6-1.2 mDa) was added to the resulting mixture and mixed at 4° C. for 10-15 min.

Hyaluronan Gel 4 (0.1M STS, 1% (w/v) Hyaluronan, Manitol)

Hyaluronan (50.09 mg; Pharma Grade 80, Kikkoman Biochemifa company; 0.6-1.2 mDa) was added to water (5 mL). Sodium thiosulfate pentahydrate (124.9 mgs) was added. The pH of the resulting mixture was adjusted to pH7.12 by addition of sodium hydroxide (1N, ca. 0.5 μL). Add appropriate amount of mannitol into the vial to adjust the osmolarity to 1.046 Osm/kg. The viscous solution was filtered through 0.22 μm Millex-GV filter.

Hyaluronan Gel 5 (0.1M STS, 1% (w/v) Hyaluronan)

Hyaluronan Gel 5 was prepared according to the procedure described for Hyaluronan Gel 1 with the exception that the amount of sodium thiosulfate pentahydrate was adjusted to provide a 0.1M concentration of sodium thiosulfate.

Hyaluronan Gel 6 (0.2M STS, 1% (w/v) Hyaluronan)

Hyaluronan Gel 6 was prepared according to the procedure described for Hyaluronan Gel 1 with the exception that the amount of sodium thiosulfate pentahydrate was adjusted to provide a 0.2M concentration of sodium thiosulfate.

Hyaluronan Gel 7 (0.3M STS, 1% (w/v) Hyaluronan)

Hyaluronan Gel 7 was prepared according to the procedure described for Hyaluronan Gel 1 with the exception that the amount of sodium thiosulfate pentahydrate was adjusted to provide a 0.3M concentration of sodium thiosulfate.

Hyaluronan Gel 8 (0.4M STS, 1% (w/v) Hyaluronan)

Hyaluronan Gel 8 was prepared according to the procedure described for Hyaluronan Gel 1 with the exception that the amount of sodium thiosulfate pentahydrate was adjusted to provide a 0.4M concentration of sodium thiosulfate.

Hyaluronan Gel 9 (0.5M STS, 1% (w/v) hyaluronan, Tris (5×))

Hyaluronan (79.99 mg; Pharma Grade 80, Kikkoman Biochemifa company; 0.6-1.2 mDa) was added to Tris buffer (8 mL, AMRESCO-0497-500G). The pH of the resulting mixture was adjusted to pH7.13 by addition of HCl (5N). Sodium thiosulfate pentahydrate (992.60 mg) was added to the above solution. The viscous solution was filtered through 0.22 μm Millex-GV filter.

Hyaluronan Gel 10 (0.5M STS, 1% (w/v) Hyaluronan, Phosphate Buffered Saline (5×))

Hyaluronan (70.38 mg; Pharma Grade 80, Kikkoman Biochemifa company; 0.6-1.2 mDa) was added to PBS buffer (7 mL, 5×). Sodium thiosulfate pentahydrate (868.46 mg) was added. The pH of the resulting mixture was adjusted to pH6.99 by addition of NaOH (1N). The viscous solution was filtered through 0.22 μM Millex-GV filter.

Hyaluronan Gel 11 (0.8M STS, 1% (w/v) Hyaluronan)

Hyaluronan Gel 11 was prepared according to the procedure described for Hyaluronan Gel 1 with the exception that the amount of sodium thiosulfate pentahydrate was adjusted to provide a 0.8M concentration of sodium thiosulfate.

Hyaluronan Gel 12 (1M STS, 0.8% (w/v) Hyaluronan)

Hyaluronan Gel 12 was prepared according to the procedure described for Hyaluronan Gel 1 with the exception that the amount of sodium thiosulfate pentahydrate was adjusted to provide a 1M concentration of sodium thiosulfate, and the amount of hyaluronan was adjusted to provide a 0.8% (w/v) concentration of hyaluronan.

Hyaluronan Gel 13 (0.5M STS, 0.82% (w/v) Hyaluronan (HYALGAN)) Hyaluronan Gel 13 was prepared by mixing of sodium thiosulfate pentahydrate with hyaluronan (HYALGAN, Fidia Pharma USA, Florham Park, N.J.) to afford the final preparation with 0.82% (w/v) concentration of hyaluronan.

Hyaluronan Gel 14 (0.5M STS, 1% (w/v) Hyaluronan (SINGCLEAN))

Hyaluronan Gel 14 was prepared according to the procedure described for Hyaluronan Gel 13 with the exception that hyaluronan (SINGCLEAN, Hangzhouh Singclean Medical Products Co., Ltd., Hangzhou, China) was used in the preparation of this gel.

Hyaluronan Gel 15 (0.5M STS, 1% (w/v) Hyaluronan (EUFLEXXA))

Hyaluronan Gel 15 was prepared according to the procedure described for Hyaluronan Gel 13 with the exception that hyaluronan (EUFLEXXA, Ferring Pharmaceuticals Inc., Parsippany, N.J.) was used in the preparation of this gel.

Hyaluronan Gel 16 (0.5M STS, 1% (w/v) Hyaluronan (HEALON))

Hyaluronan Gel 16 was prepared according to the procedure described for Hyaluronan Gel 13 with the exception that hyaluronan (HEALON, Johnson & Johnson, New Brunswick, N.J.) was used in the preparation of this gel.

Hyaluronan Gel 17 (1M STS, 1% (w/v) Hyaluronan)

Hyaluronan Gel 17 was prepared according to the procedure described for Hyaluronan Gel 1 with the exception that the amount of sodium thiosulfate pentahydrate was adjusted to provide a 1M concentration of sodium thiosulfate.

Hyaluronan Gel 18 (10% (w/v) N-Acetyl-L-Cysteine, 1% (w/v) Hyaluronan)

Hyaluronan (39.38 mg; Pharma Grade 80, Kikkoman Biochemifa company; 0.6-1.2 mDa) was added to water (4 mL). N-Acetyl-L-cysteine (399.14 mg) was added. The pH of the resulting mixture was adjusted to pH 7.21 by addition of NaOH (10N, 240 µL). The viscous solution was filtered through 0.22 µM Millex-GV filter. The osmotic pressure was measured as 1.107 Osm/kg.

Other hyaluronan gels may be prepared using the procedures described herein. For example, 1M and 1.5M hyaluronan gels may be prepared according to the same procedure as described for, e.g., Hyaluronan Gel 1 and Hyaluronan Gel 12. Additionally, pH levels of the gels may be adjusted to pH 6.5 to 8.5 using Brønsted acids (e.g., hydrochloric acid) and bases (e.g., sodium hydroxide).

Example 2. Pharmacokinetics

Guinea Pigs, Study 1

Albino guinea pigs (Hartley), body weight at 250-350 g, were used for the studies. For dosing, the animal was placed on its shoulder with the surgery ear up and auditory bulla was first exposed using retroauricular approach. A hole of 2-3 mm in diameter was drilled on the bulla to provide direct visualization of the round window niche. Then, 10 µL of an aqueous composition of 0.5M sodium thiosulfate/2% (w/v) hyaluronan (STS Composition) were applied onto the RWM using a 10 µL Hamilton syringe and a 26-gauge needle. After application, guinea pigs remained at this position for 30 min to allow compound to diffuse into the cochlea. The bulla opening was sealed with a muscle graft and the incision closed with sutures.

Sampling procedures are as follows, in brief. All sampling procedures are terminal. Animals were euthanized with $CO_2$. 0.5 mL samples of blood were collected by cardiac puncture. Plasma was separated by centrifugation at 5,000 rpm at 4° C. for 10 min and collected in a separate tube. 50 µL of cerebrospinal fluid were collected through the cisterna magma. Perilymph was collected ex vivo to avoid contamination from the cerebrospinal fluid influx via the cochlear aqueduct. The temporal bone was rapidly isolated, and the bulla was removed to expose the cochlea. Any visible remaining dosed compositions were carefully removed with absorbent points under the surgical microscope before perilymph sampling. A small hole was made at the apex, and then 5-7 µL of perilymph was sampled using a pulled glass pipette. All samples were frozen immediately on dry ice and stored in −80° C. until analysis. The concentrations of thiosulfate in the samples were measured using the method disclosed in Togawa et al. *Chem. Pharm. Bull.*, 40:3000-3004, 1992, the disclosure of which is incorporated herein by reference. The results of this study are shown in FIGS. 1A, 1B, 2A, and 2B and in Table 1.

Cynomolgus Monkey

Cynomolgus monkey was administered tolfedine (4 mg/kg) subcutaneously. After 30 minutes, the animal was anesthetized via intravenous bolus of propofol (5.5 mg/kg). 2-3% isoflurane inhalation was then used to maintain the animal in anesthetized state. The animal was then immobilized and placed laterally in reverse Trendelenburg position to ensure the access to the round window. During the surgery process, the animal was kept on a warm blanket.

Intratympanic injection in right ear was conducted when the animal reaches the anesthetized state. 1.1 mL of epinephrine hydrochloride-saline (0.1 mg in 10 mL saline) and 0.5 mL of lidocaine hydrochloride (20 mg/mL) were injected subcutaneously into the skin of ear canal posterior wall of each ear respectively as local anesthetics. An incision was then made in the post-auricular skin, and part of the temporal bone was drilled to expose middle ear. 50 µL of the STS composition were injected into the round window membrane using a 25G needle. After dosing, the animal was left on a line with its head up to allow the dosing solution to settle into the tympanic cavity for 30 mins. The same procedure was then repeated for the opposite ear.

Plasma and CSF were collected ca. 2 h after dosing the $1^{st}$ ear (right). Right ear cochlea perilymph sampling was conducted ca. 3 h after the right ear dosing. The animal was euthanized by IV administration of propofol at 11 mg/kg and then exsanguinated via femoral artery. Animal was then placed in lateral recumbent. A post-auricular skin incision was made and the external ear canal was extracted to expose middle ear. Part of the temporal bone was then drilled to expose the basal turn of the cochlea. The remaining dose in the middle ear (if visible) was cleaned with cotton tips. A drop of tissue glue was spread at the base of the cochlea to minimize the contamination from the dosed compositions.

Using a 0.5-1 mm round-tipped burr or sharped crochet, a hole was made at the basal turn of cochlea. Perilymph (ca. 10 µL) was then collected using the capillary tube inserted into the cochlear scala tympani. The same procedure was repeated for the left ear cochlea perilymph sampling ca. 2 h after the left ear dosing. The results of this study are shown in Table 1.

TABLE 1

|  | Poloxamer 407 gel 1 | Hyaluronan Gel 2 | Hyaluronan Gel 3 | Hyaluronan Gel 1 | Hyaluronan Gel 1 | Hyaluronan Gel 1 |
| --- | --- | --- | --- | --- | --- | --- |
| Species | Guinea Pig | Guinea Pig | Guinea Pig | Guinea Pig | Guinea Pig | Cynomolgus Monkey |
| Dose | 10 µL (IT) | 10 µL (IT) | 10 µL (IT) | 10 µL (IT) | 50 µL (TT) | 50 µL (IT) |
| Total Dose (mg) | 0.11 | 0.11 | 0.56 | 0.56 | 2.8 | 2.8 |
| Tmax (est.) (h) | 1 | 1 | 3 | 1.8 | 1 |  |
| Cmax (ng/mL) | 59000 | 104040 | 712800 | 1686200 | 1930000 | 688500 @ 2 h |
| Terminal t(½) (h) | 2.38 | 1.53 | 2.66 | 2.01 | 2.73 |  |
| AUC last (h · ng/mL) | 212523 | 327512 | 4634845 | 9069083 | 10498230 |  |
| AUC inf (h · ng/mL) | 255707 | 377265 | 4724413 | 10418954 | 10703165 |  |
| Plasma* (ng/mL) |  |  |  |  | 2390 | 766 |

In the above table, IT is intratympanic administration, and TT is transtympanic administration.
*concentration of thiosulfate as measured in plasma samples from the tested animals.

Guinea Pigs, Study 2

Male guinea pigs weighing 200-300 g of approximately 5-7 weeks of age served as subjects (N=5 per group). Prior to any procedures, animals were anesthetized using zolazepam hydrochloride (Zoletil 50; 20 mg/kg) 10 minutes before surgery via the intramuscular route. If needed, an intraoperative booster was administered intraperitoneally representing a one-tenth of the original dose.

Intratympanic Injection:

1. Under microscopic magnification, sharp scissors were used to create a 0.5-1.5 cm postauricular skin incision, approximately 6-8 mm caudal to the auriculo-cephalic crease. Care was exercised to avoid cutting deeply to preserve underlying vascular structures.
2. Careful blunt dissection through the subcutaneous fat layer, muscles and tissues was performed with forceps. The cleidomastoideus muscle body was gently retracted until the shiny dome of the tympanic bulla periosteum came into view. At the caudal aspect of the bulla, the insertion of a deeper cervical muscle, the sternomastoideus came into view. The facial nerve, which becomes visible at the dorsal and rostral aspect of the bulla dome, was preserved during the operation.
3. A self-retaining retractor was placed prior to creating a small hole (0.5 mm diameter) either with a drilling in the posterior part of the bulla. The bulla bone was uncapped in a dorsal and caudal direction using a pair of jeweler's tip forceps. The bone was removed in a piecemeal fashion under high magnification. Care was exercised not to puncture the stapedial artery, which lies directly beneath the bulla cap, as bleeding from this artery may compromise the procedure. The amount of bone removed was kept to a minimum to prevent excessive fluid entry to the middle ear while still allowing excellent visualization and access to the round window niche.
4. 10 or 90 µL of a gel formulation was delivered to the round window niche using a sterile glass Hamilton syringe with 25-26 G blunt needle.
5. The delivered agent was allowed to rest within the round window niche for up to 30 min. The small hole was covered with muscular tissue and tissue glue.
6. The incision was closed with sutures (4-0 non-absorbable monofilament or 5-0 non-absorbable nylon) and tissue glue or wound clips. The entire procedure took approximately 3-5 minutes depending on agent specifications.
7. During the procedure and until recovery, animals were placed on a temperature controlled (38° C.) heating pad until consciousness was regained, at which time they were returned to the home-cage.

Alternatively, the animals were administered the gel formulations transtympanically.

Sampling Collection:

Blood Collection:

1. Without preinflating in the euthanasia box, the guinea pig was placed in a box, and 100% carbon dioxide was introduced to cause the animal unconsciousness and to reduce animal suffering. Carbon dioxide flow was maintained for a minimum of 1 minute after the breath has stopped. The guinea pig was removed from the euthanasia box after death was confirmed.
2. Blood was collected immediately after euthanasia.
3. After the operator fixed the animal's back position, the needle was inserted at the front of the sternal ridge at 4-6 or slightly forward.
4. The needle was pulled back, and the blood was returned.
5. Volume: for each blood collection, ca. 1 mL of blood was collected.

CSF Collection:

CSF was collected after euthanasia. A 0.5*20 intravenous infusion needle was slowly lowered from 90° to the foramen magnum. The needle reached a distance of 4.5-5 mm under the skin, and 50-200 µl of clear tissue fluid were withdrawn.

Perilymph Collection:

After euthanasia, the animal was stripped excess skin and muscle tissue to obtain a complete auditory bulla, and the bulla wall was cut with small forceps to expose the cochlea. The basal turn of bulla was cleaned by using small cotton ball. The cochlear bottom circle and the round window were coated with bio glue. After drying, a unique microhole was hand-drilled in the top circle of the cochlea. A 2 µL volume of perilymph was then collected using a microcapillary inserted into the cochlear top circle. Perilymph samples were added to a vial containing 18 µL of bovine serum albumin (BSA, 1M) stored at −80° C. until analysis.

The results of the Guinea Pig, Study 2 are provided in Tables 2 and 3.

TABLE 2

| Formulation | Route | $T_{max}$ (h) | $C_{max}$ (ng/mL) | terminal $T_{1/2}$ (h) | $AUC_{INF}$ (h × ng/g) | $AUC_{last}$ (h × ng/g) | Osmol. (Osm/kg) |
|---|---|---|---|---|---|---|---|
| Hyaluronan Gel 1 | TT (50 μL) | 1 | 872360 | 2.73 | 4837831 | 4745200 | |
| Hyaluronan Gel 4 | TT (50 μL) | 3 | 115300 | 2.3 | 608881 | 601694 | 1.046 |
| Hyaluronan Gel 5 | TT (50 μL) | 1 | 391432 | 6.42 | 4084991 | 3529898 | 0.267 |
| Hyaluronan Gel 6 | TT (50 μL) | 1 | 1069794 | 8.89 | 5727631 | 4150041 | |
| Hyaluronan Gel 6* | TT (50 μL) | 3 | 500900 | N/A | N/A | 3817583 | 0.491 |
| Hyaluronan Gel 7 | TT (50 μL) | 7 | 210933 | N/A | | 2357105 | 0.657 |
| Hyaluronan Gel 7* | TT (50 μL) | 3 | 600420 | N/A | N/A | 3281800 | 0.66 |
| Hyaluronan Gel 8 | TT (50 μL) | 1 | 508500 | 3.48 | 4014647 | 3887550 | 0.838 |
| Hyaluronan Gel 9 | TT (50 μL) | 1 | 1602936 | 2.11 | 7029505 | 6990442 | 2.048 |
| Hyaluronan Gel 10 | TT (50 μL) | 1 | 1293624 | 2.2 | 5866461 | 5825930 | |
| Hyaluronan Gel 11 | TT (50 μL) | 1 | 1371800 | 2.99 | 5863793 | 5714356 | 1.494 |
| Hyaluronan Gel 12 | TT (50 μL) | 1 | 1892000 | 2.57 | 7744025 | 7644025 | 1.860 |
| Hyaluronan Gel 17 | TT (50 μL) | 1 | 1044400 | 2.47 | 5918627 | 5843593 | |
| Hyaluronan Gel 18 | TT (50 μL) | 1 | 705600 | 5.53 | 4887980 | 4876589 | 1.107 |

In this table, TT is transtympanic administration,
*This test was a duplicate of the preceding test.

TABLE 3

| Formulation | MW (mDa) | Route | $T_{max}$ (h) | $C_{max}$ (ng/mL) | terminal $T_{1/2}$ | $AUC_{INF}$ (h × ng/g) | $AUC_{last}$ (h × ng/g) |
|---|---|---|---|---|---|---|---|
| Hyaluronan Gel 1 | 0.6-1.2 | IT (10 μL) | 1 | 625297 | 1.88 | 4112197 | 4099226 |
| Hyaluronan Gel 13 | 0.5-0.73 | TT (50 μL) | 1 | 815408 | 2.82 | 4868652 | 4754315 |
| Hyaluronan Gel 14 | unknown | TT (50 μL) | 1 | 851568 | 3.27 | 5178077 | 4992602 |
| Hyaluronan Gel 15 | 2.4-3.6 | TT (50 μL) | 1 | 628200 | 3.41 | 3908302 | 3761700 |
| Hyaluronan Gel 16 | ca. 4 | TT (50 μL) | 1 | 919097 | 5.42 | 5033151 | 4407366 |

In this table, IT is intratympanic administration, and TT is transtympanic administration.

Example 3. Pharmacodynamics

Cisplatin was diluted with 0.9% (w/v) saline to a final concentration of 5 mg/mL. Albino guinea pigs (Hartley), body weight at 250-350 g were used in the study. After a minimal 3 days acclamation, 28 animals were enrolled into the study. Under aseptic condition, cisplatin was administered intraperitoneally with a bolus injection. The five cohorts were staggered with different starting dates for the study.

Seven days after the cisplatin administration, the animals were recorded for their auditory brainstem responses (ABR) response using TDT RZ6 Multi-I/O processor. Historical ABR data were used to define a baseline. The animals were anesthetized with tiletamine hydrochloride and zolazepam hydrochloride (Zoletil). Acoustic stimuli were delivered via an earphone. Needle electrodes were placed near the ear canal at the causoventral position, the vertex of the skull, and a ground at the lower leg. The stimulus level was from 10 to 90 dB in 5 dB steps, and the tone-pip frequencies were 4, 24, and 32 kHz. The ceiling sound pressure level was 90 dB. ABR threshold was observed by visual inspection of stacked waveforms as the lowest sound pressure level, at which the waveform was above the noise floor.

Prior to the cisplatin study, ABR data from 50 animals were recorded for both ears of each animal (Naïve n=100). The threshold at 32 kHz in naïve animals was 39.8 dB. The range of normal hearing was defined as a mean±2SD, 27.9 to 51.6 dB. Cisplatin primarily induces hearing loss at high frequencies. A clear pattern of hearing loss after cisplatin is defined as a threshold of 60 dB and above at 32 kHz.

Figure 3A:
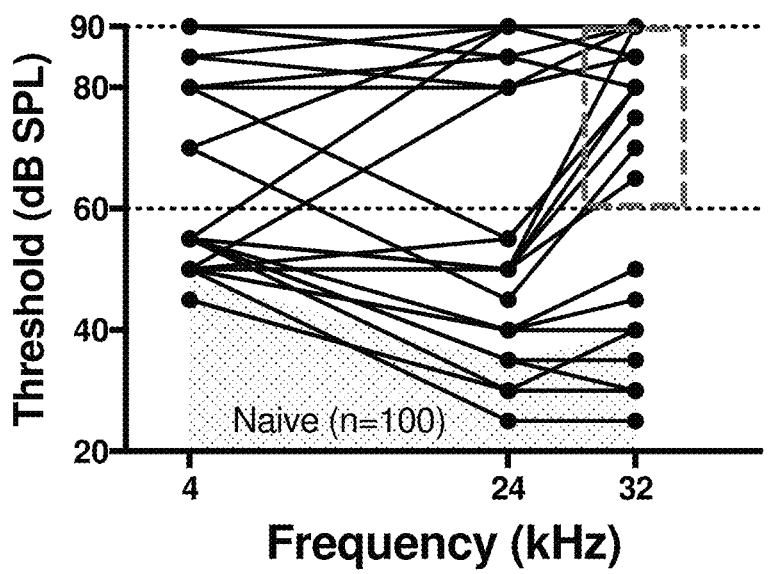
FIG. 3A is a chart showing the threshold sound pressure levels at 4, 24, and 32 kHz measured across five cohorts of guinea pigs (n=27 animals) during auditory brainstem response tests. Seven days prior to the auditory brainstem response tests, all guinea pigs were injected intraperitoneally with a bolus of cisplatin. The baseline thresholds were from historic auditory brainstem response tests on cisplatin-naïve guinea pigs (n=100 ears). The baseline thresholds are shown as a shaded area curve.
Figure 3B:
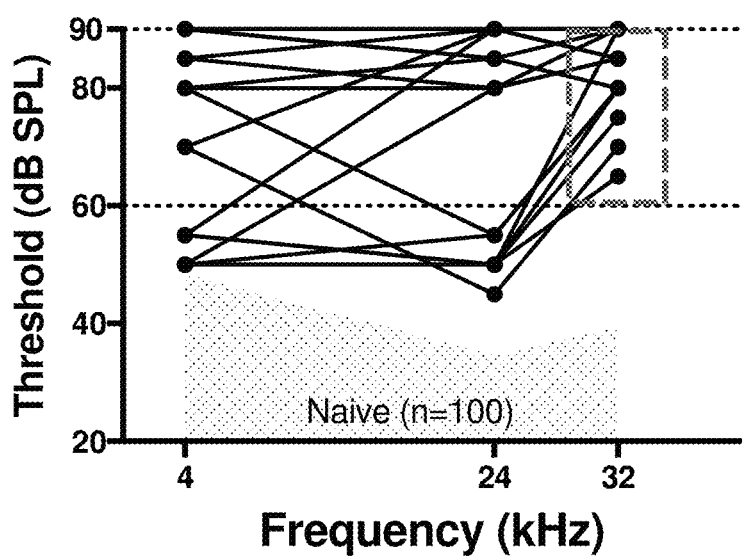
FIG. 3B is a chart showing the threshold sound pressure levels at 4, 24, and 32 kHz measured during auditory brainstem response tests for the guinea pigs deemed to have hearing loss (n=18 animals). Seven days prior to the auditory brainstem response tests, all guinea pigs were injected intraperitoneally with a bolus of cisplatin. The baseline thresholds were from historic auditory brainstem response tests on cisplatin-naïve guinea pigs (n=100 ears). The baseline thresholds are shown as a shaded area curve.
Figure 4A:
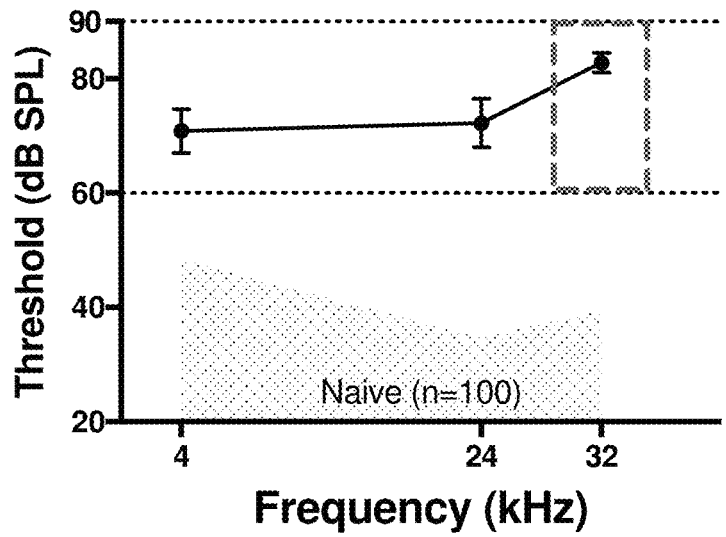
FIG. 4A is a chart showing the average threshold sound pressure levels at 4, 24, and 32 kHz measured during auditory brainstem response tests for the guinea pigs deemed to have hearing loss (n=18 animals). Seven days prior to the auditory brainstem response tests, all guinea pigs were injected intraperitoneally with a bolus of cisplatin. The baseline thresholds were from historic auditory brainstem response tests on cisplatin-naïve guinea pigs (n=100 ears). The baseline thresholds are shown as a shaded area curve.

In this study, 1 out of 28 animals died before the day 7 measurement. In the remaining 27 animals, 18 animals had hearing loss with threshold >60 dB at 32 kHz (FIG. 3A). The range of hearing loss at 32 kHz was the thresholds from 65 dB to 90 dB (FIG. 3B). 90 dB is the measurement ceiling. Note when no waveform or waveform only seen at 90 dB, the threshold was defined both as 90 dB. The average threshold at 32 kHz was 82 dB, which corresponds to an average 42.2 dB shift from the naïve threshold of 39.8 dB (FIG. 4A).

Local Intratympanic Dosing and Cochlear Sampling

Local intratympanic dosing and cochlear sampling were conducted as described in Example 2.

Locally Delivered Anti-Platinum Chemoprotectant Agent Provides Hearing Protection from Platinum-Based Antineoplastic Agent Evaluation of the effect of a locally delivered anti-platinum chemoprotectant agent on hearing protection from a platinum-based antineoplastic agent was conducted as follows.

Figure 5:
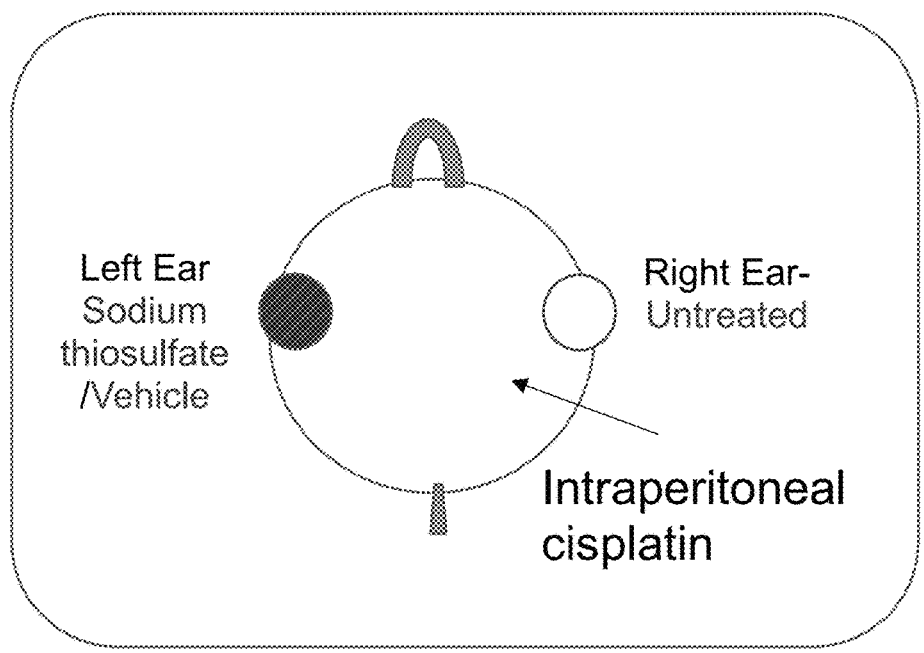
FIG. 5 is a figure illustrating the cisplatin challenge test following administration of vehicle or sodium thiosulfate to one ear of a guinea pig.

An aqueous composition of 0.5M sodium thiosulfate/2% (w/v) hyaluronan (STS Composition) or vehicle was dosed intratympanically onto the round window in the left ear (LE) as described above, and the right ear (RE) was left untreated in the guinea pigs (FIG. 5). 60 min after STS Composition or vehicle dosing, the animals were injected with cisplatin at 10 mg/kg intraperitoneally. ABR at 4, 24, and 32 kHz was measured in both ears 7 days after cisplatin administration.

Figure 4B:
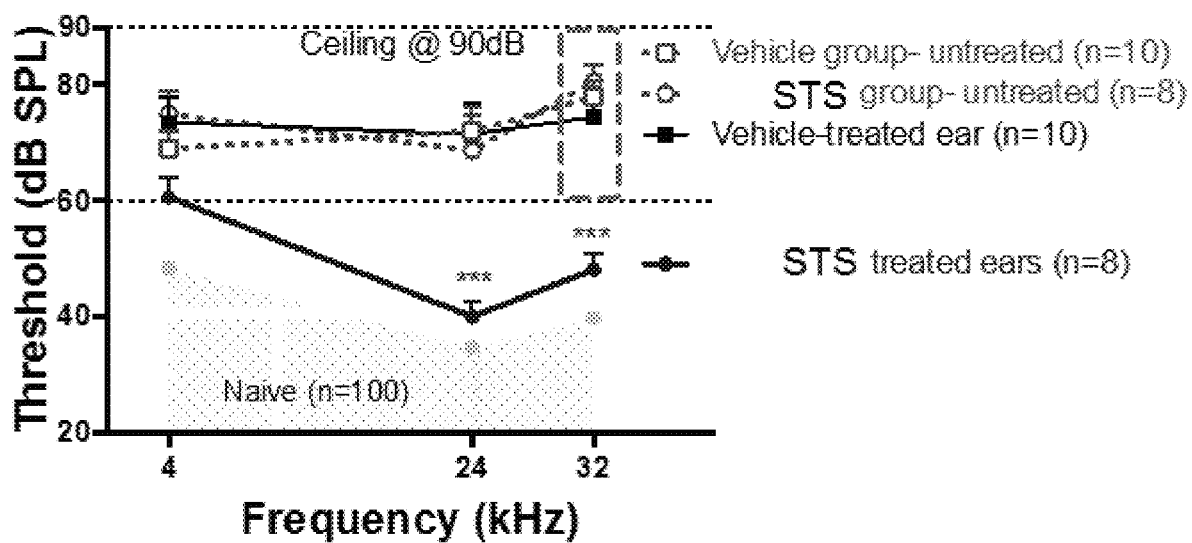
FIG. 4B is a chart showing the average threshold sound pressure levels at 4, 24, and 32 kHz measured during auditory brainstem response (ABR) tests for the guinea pigs administered vehicle or sodium thiosulfate to one ear each followed by a cisplatin challenge. The baseline thresholds were from historic auditory brainstem response tests on cisplatin-naïve guinea pigs (n=100 ears). The baseline thresholds are shown as a shaded area curve.

Because of heterogenity of hearing loss after cisplatin challenge, the untreated right ears was used to select the animals with hearing loss. There were 21 animals with right ear threshold >60 dB at 32 kHz. Of these 21 animals, 3 with otitis media were excluded, leaving 18 animals for the final analysis. 10 animals were dosed with vehicle and 8 animals were dosed with STS Composition (FIG. 4B). In the untreated right ears of both the STS Composition and vehicle groups, there is no difference in the ABR thresholds with an average threshold 73 dB at 4 kHz, 71 dB at 24 kHz, and 80 dB at 32 kHz. The vehicle-treated left ears had no significant difference in comparison to their untreated right ears, showing thresholds 74 dB at 4 kHz, 70 dB at 24 kHz, and 74 dB at 32 kHz.

The STS Composition-treated ears had significantly lower thresholds at both 32 kHz and 24 KHz compared to the vehicle-treated ears and untreated right ears (***P<0.001, two way ANOVA). At 4 kHz an average threshold was 61 dB in the STS Composition treated ears and 75 dB in their untreated contralateral right ears; the protection was not statistically significant (P=0.089). The average thresholds in the STS Composition treated ears were 40 dB and 48 dB at 24 kHz and 32 kHz, respectively, in contrast to 69 dB and 80 dB in their contralateral untreated right ears. The normal hearing thresholds were 35 dB and 40 dB at 24 kHz and at 32 kHz, respectively, in the naïve animals. To the naïve ears, the untreated ears after cisplatin had an average of 34 dB and 40 dB threshold elevation at 24 kHz and 32 kHz, respectively, but STS Composition treated ears only had 5 dB and 8 dB shift. Therefore, sodium thiosulfate provided, on average, 80% protection at both 24 kHz and 32 kHz.

Figure 6:
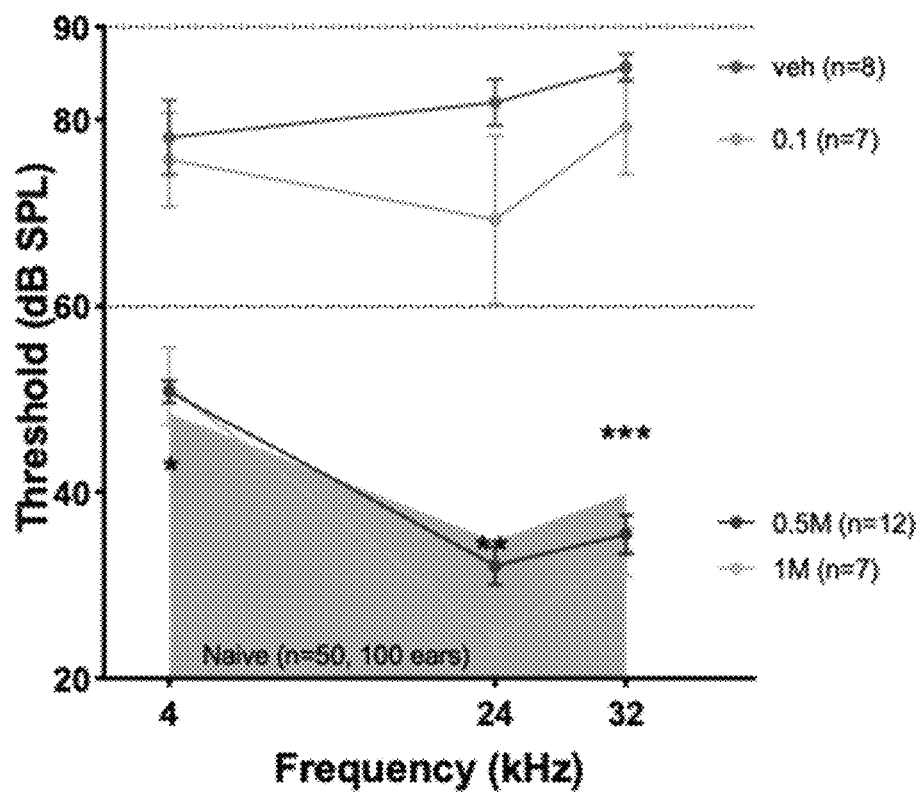
FIG. 6 is a chart showing the average threshold sound pressure levels at 4, 24, and 32 kHz measured during auditory brainstem response (ABR) tests for the guinea pigs administered vehicle or sodium thiosulfate (0.1M, 0.5M, or 1M sodium thiosulfate gel) to one ear each followed by a cisplatin challenge. The baseline thresholds were from historic auditory brainstem response tests on cisplatin-naïve guinea pigs (n=100 ears). The baseline thresholds are shown as a shaded area curve.

In a similarly designed study as described hereinabove, sound pressure levels at 4, 24, and 32 kHz were measured during ABR tests for the guinea pigs administered vehicle or sodium thiosulfate (0.1M, 0.5M, or 1M sodium thiosulfate gel) to one ear each followed by a cisplatin challenge (Cisplatin 10MPK, intravenous injection). Different doses of hyaluronan gels were administered as a 10 µL IT injection into the left ear one hour prior to cisplatin administration. The contralateral ear (right ear) of the animal was untreated. Hyaluronan Gel 5 (0.1M), Hyaluronan Gel 1 (0.5M), and Hyaluronan Gel 17 (1M) was tested. The untreated ears demonstrated significant threshold shifts compared to naïve animals (gray shaded areas). The groups treated with Hyaluronan Gel 1 (0.5M) and Hyaluronan Gel 17 (1M) showed hearing protection compared to the untreated contralateral control ears at all tested frequencies. No protection was seen with the vehicle treated ears. The results are summarized in FIG. 6.

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A hypertonic pharmaceutical composition having a calculated osmolarity of 1,500-7,000 mOsm/L and comprising 0.5M-2.0M of an anti-platinum chemoprotectant agent, a gelling agent, and an optional tonicity agent; wherein the calculated osmolarity is calculated based on the chemoprotectant agent and the tonicity agent, if present.

2. The hypertonic pharmaceutical composition of claim 1, wherein the calculated osmolarity of the composition is at least 2,000 mOsm/L.

3. The hypertonic pharmaceutical composition of claim 1, wherein the anti-platinum chemoprotectant agent is an alkaline or ammonium thiosulfate salt or a solvate thereof, an alkaline diethyldithiocarbamate salt, amifostine, methionine, N-acetylcysteine, cysteine, 2-aminoethanethiol, glutathione (GSH) or a $C_1$-$C_6$ alkyl ester thereof, lysine, histidine, arginine, ethylene diamine tetraacetic acid, dimercaprol, dimercaptosuccinic acid, dimercapto-propane sulfonate salt, penicillamine, α-lipoic acid, or fursultiamine, or a salt thereof.

4. The hypertonic pharmaceutical composition of claim 3, wherein the alkaline thiosulfate salt is sodium thiosulfate or a solvate thereof.

5. The hypertonic pharmaceutical composition of claim 1, wherein the gelling agent is hyaluronan, a polyoxyethylene-polyoxypropylene block copolymer, poly(lactic-co-glycolic) acid, polylactic acid, polycaprolactone, alginic acid or a salt thereof, polyethylene glycol, a cellulose, a cellulose ether, a carbomer, agar-agar, gelatin, glucomannan, galactomannan, xanthan gum, chitosan, pectin, starch, tragacanth, carrageenan, polyvinylpyrrolidone, polyvinyl alcohol, paraffin, petrolatum, silicates, fibroin, or a combination thereof.

6. The hypertonic pharmaceutical composition of claim 5, wherein the gelling agent is hyaluronan.

7. The hypertonic pharmaceutical composition of claim 6, further comprising a pharmaceutically acceptable liquid solvent, wherein the pharmaceutically acceptable liquid solvent is water.

8. The hypertonic pharmaceutical composition of claim 7, wherein the hypertonic pharmaceutical composition comprises at least about 0.8% (w/v) of the gelling agent relative to the liquid solvent.

9. The hypertonic pharmaceutical composition of claim 1, wherein the concentration of the anti-platinum chemoprotectant agent is 0.5M-1.5M.

10. The hypertonic pharmaceutical composition of claim 1, wherein the pH of the pharmaceutical composition is 6.5 to 8.5.

11. The hypertonic pharmaceutical composition of claim 1, wherein the hypertonic pharmaceutical composition is a pharmaceutical dosage form.

12. A method of preventing or mitigating platinum-induced ototoxicity in a subject, the method comprising administering to the round window of the subject an effective amount of the hypertonic pharmaceutical composition of claim 11.

13. A method of preparing the hypertonic pharmaceutical composition of claim 11, the method comprising (i) providing the anti-platinum chemoprotectant agent, the gelling agent, and the optional tonicity agent, and (ii) mixing the anti-platinum chemoprotectant agent, the gelling agent, and the optional tonicity agent with a pharmaceutically acceptable liquid solvent to produce the hypertonic pharmaceutical composition.

14. The hypertonic pharmaceutical composition of claim 1, wherein the hypertonic pharmaceutical composition comprises a pharmaceutically acceptable liquid solvent and 0.8M-2.0M of the anti-platinum chemoprotectant agent.

15. The hypertonic pharmaceutical composition of claim 14, wherein the anti-platinum chemoprotectant agent is sodium thiosulfate or a solvate thereof.

16. The hypertonic pharmaceutical composition of claim 14, wherein the hypertonic pharmaceutical composition comprises at least about 0.8% (w/v) of the gelling agent relative to the liquid solvent.

17. The hypertonic pharmaceutical composition of claim 16, wherein the gelling agent is hyaluronan.

18. The hypertonic pharmaceutical composition of claim 14, wherein the calculated osmolarity of the composition is at least 2,500 mOsm/L.

19. The hypertonic pharmaceutical composition of claim 17, wherein the anti-platinum chemoprotectant agent is sodium thiosulfate or a solvate thereof.

20. The hypertonic pharmaceutical composition of claim 1, wherein
the hypertonic pharmaceutical composition comprises at least about 0.8% (w/v) of the gelling agent relative to the liquid solvent;
the gelling agent is hyaluronan; and
the anti-platinum chemoprotectant agent is sodium thiosulfate or a solvate thereof.

21. The hypertonic pharmaceutical composition of claim 20, wherein the hypertonic pharmaceutical composition comprises 0.8M-2.0M of the anti-platinum chemoprotectant agent.

22. The hypertonic pharmaceutical composition of claim 8, wherein the hypertonic pharmaceutical composition comprises about 0.8% to about 2% (w/v) of the gelling agent relative to the liquid solvent.

23. The hypertonic pharmaceutical composition of claim 1, wherein the hypertonic pharmaceutical composition is formulated for administration to the round window of a human and has a volume of 200 μL to 1 mL.

24. The hypertonic pharmaceutical composition of claim 22, wherein the hypertonic pharmaceutical composition is formulated for administration to the round window of a human and has a volume of 200 μL to 1 mL.

25. The method of claim 12, wherein the effective amount is 200 μL to 1 mL of the hypertonic pharmaceutical composition.

26. The method of claim 25, wherein the subject is a subject receiving a platinum-based antineoplastic agent.

27. The method of claim 26, wherein the gelling agent is hyaluronan and the anti-platinum chemoprotectant agent is sodium thiosulfate or a solvate thereof.

28. A hypertonic pharmaceutical composition having a calculated osmolarity of 1,500-7,000 mOsm/L and comprising 0.5M-2.0M of an anti-platinum chemoprotectant agent and a gelling agent.

29. The hypertonic pharmaceutical composition of claim 28, wherein
the anti-platinum chemoprotectant agent is sodium thiosulfate or a solvate thereof,
the gelling agent is hyaluronan,
the hypertonic pharmaceutical composition further comprises a liquid solvent, and
the hypertonic pharmaceutical composition comprises about 0.8% to about 2% (w/v) of hyaluronan relative to the liquid solvent.

30. The hypertonic pharmaceutical composition of claim 29, wherein the hypertonic pharmaceutical composition is formulated for administration to the round window of a human and has a volume of 200 μL to 1 mL.

31. A hypertonic pharmaceutical composition having a calculated osmolarity of at least 1,500 mOsm/L and comprising 0.5M-2.0M of an anti-platinum chemoprotectant agent, a gelling agent, and an optional tonicity agent; wherein the calculated osmolarity is calculated based on the chemoprotectant agent and the tonicity agent, if present.

32. The hypertonic pharmaceutical composition of claim 31, wherein
the anti-platinum chemoprotectant agent is sodium thiosulfate or a solvate thereof,
the gelling agent is hyaluronan,
the hypertonic pharmaceutical composition further comprises a liquid solvent, and
the hypertonic pharmaceutical composition comprises about 0.8% to about 2% (w/v) of hyaluronan relative to the liquid solvent.

33. The hypertonic pharmaceutical composition of claim 32, wherein the hypertonic pharmaceutical composition is formulated for administration to the round window of a human and has a volume of 200 μL to 1 mL.

* * * * *